United States Patent [19]
Whittaker et al.

[11] Patent Number: 5,906,922
[45] Date of Patent: May 25, 1999

[54] DELIVERY OF NUCLEIC ACIDS

[75] Inventors: Robert George Whittaker, West Pymble; Fiona Helen Cameron, Lindfield; Veronika Bender, Cremorne; Minoo Moghaddam, Killara; Philip Anthony Jennings, Brookfield, all of Australia

[73] Assignee: Commonwealth Scientific and Industrial Research Organisation, Parkville, Australia

[21] Appl. No.: 08/776,908

[22] PCT Filed: Aug. 16, 1995

[86] PCT No.: PCT/AU95/00505

§ 371 Date: Apr. 16, 1997

§ 102(e) Date: Apr. 16, 1997

[87] PCT Pub. No.: WO96/05218

PCT Pub. Date: Feb. 22, 1996

[30] Foreign Application Priority Data

Aug. 16, 1994 [AU] Australia ................................ PM7476
Aug. 25, 1994 [AU] Australia ................................ PM7677

[51] Int. Cl.$^6$ ............................ C12P 21/02; C07C 53/00; C07C 229/00; C12N 15/64
[52] U.S. Cl. .................. 435/69.1; 435/172.1; 514/44; 554/1; 554/103; 554/124; 554/227
[58] Field of Search ............................. 514/44; 435/69.1, 435/172.1; 554/1, 103, 124, 227

[56] References Cited

U.S. PATENT DOCUMENTS 5,264,618  11/1993  Felgner et al. ............................ 524/495
5,329,029  7/1994   Wan et al. ................................ 554/80

FOREIGN PATENT DOCUMENTS 424688     5/1991   European Pat. Off. .
475178     3/1992   European Pat. Off. .
WO91/09837 7/1991   WIPO .
WO91/15501 10/1991  WIPO .
WO93/02706 2/1993   WIPO .
WO93/07883 4/1993   WIPO .
WO93/12756 7/1993   WIPO .
WO94/23738 10/1994  WIPO .
WO95/04030 2/1995   WIPO .

OTHER PUBLICATIONS

Newkome et al. "Polytryptophane terminated dendritic macromolecules," *Tetrahedron: Asymmetry*, v.2, pp. 975–960.

Orkin et al "Report & Recommendations of the Panel to Assess The NIH Investment in Research on Gene Therapy", 1995.

Fiani et al "Selective Targeting of Drugs" TIBTECH vol. 7 57–61, 1989.

*Primary Examiner*—Nancy Degen
*Attorney, Agent, or Firm*—McDermott, Will & Emery

[57] ABSTRACT

The present invention provides a method for introducing nucleic acids into cells. The method involves exposing the cells to a compound having formula (1), in which w is a nucleic acid, x is a peptide or amino acid, y is a linker having a chain length equivalent to 1 to 20 carbon atoms or is absent, $R_4$ is H ir $CH_2O$—$R_3$; and $R_1$, $R_2$ and $R_3$ are the same or different and are either hydrogen, methyl, ethyl, hydroxyl or an acyl group derived from a fatty acid having a carbon chain of 3 to 24 carbon atoms saturated or unsaturated, with the proviso that at least one of $R_1$, $R_2$ and $R_3$ is an acyl group derived from a fatty acid, or to a compound having the formula (2): w . . . xyNHCH$_2$CH$_2$OR$_5$, in which w is a nucleic acid, x is a peptide or amino acid, y is a linker having a chain length equivalent to 1 to 20 carbon atoms or absent, $R_5$ is an acyl group derived from a fatty acid having a carbon chain of 3 to 24 carbon atoms saturated or unsaturated. The invention also relates to these compounds.

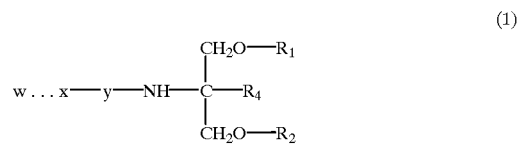

(1)

56 Claims, 21 Drawing Sheets

CHO CELLS

Cos 1 CELLS

PC3 CELLS

JURKAT CELLS

DELIVERY OF NUCLEIC ACIDS

BACKGROUND OF THE INVENTION

The present invention relates to a method of introducing compounds, in particular nucleic acids, into cells. Further, the present invention relates to compositions for use in this method.

There are a number of situations in which it is desirable to deliver specific compounds into cells. One of these applications is the transfection of eucaryotic cells with DNA. This is currently done using various commercial agents such as "Transfectam" (Promega), "DOTAP", (Boehringer Mannheim), "Lipofectin" or "Lipofectamine" (BRL), or by using calcium phosphate mediated transfection.

The ability to deliver nucleic acid based compounds to cells also has application in drug delivery and gene therapy. The delivery of compounds into cells will change in association with a compound of the formula described below. Such changes may be manifested as modifications to their duration of action, (e.g. slow release or sustained action) the amount of drug required or the mode of delivery. Delivery into cells using compounds variant within the parameters described below may also enable cell or tissue-specific targeting of drugs.

The present inventors have found that association of molecules with compounds modified with fatty acid acyl derivatives, of the general formula below, facilitates delivery of those compounds into cells.

SUMMARY OF THE INVENTION

Accordingly, in a first aspect the present invention consists of a method for introducing nucleic acid into a cell comprising exposing the cell to a compound having the formula:

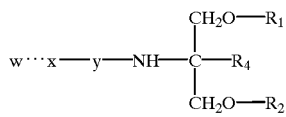

in which:
  w is a nucleic acid
  x is a peptide or amino acid
  y is a linker having a chain length equivalent to 1 to 20 carbon atoms or is absent
  $R_4$ is H or $CH_2O$—$R_3$; and $R_1$, $R_2$ and $R_3$ are the same or different and are either hydrogen, methyl, ethyl, hydroxyl or an acyl group derived from a fatty acid having a carbon chain of 3 to 24 carbon atoms saturated or unsaturated, with the proviso that at least one of $R_1$, $R_2$ and $R_3$ is an acyl group derived from a fatty acid.

In a second aspect the present invention consists of a method for introducing nucleic acid into a cell comprising exposing the cell to a compound having the formula:

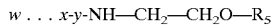

in which:
  w is a nucleic acid
  x is a peptide or amino acid
  y is a linker having a chain length equivalent to 1 to 20 carbon atoms or is absent
  $R_5$ is an acyl group derived from a fatty acid having a carbon chain of 3 to 24 carbon atoms saturated or unsaturated.

In a third aspect the present invention consists in a compound for use in introducing nucleic acid into a cell, the compound having the formula

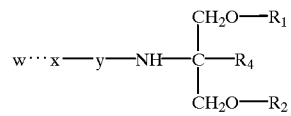

in which:
  w is a nucleic acid
  x is a peptide or amino acid
  y is a linker having a chain length equivalent to 1 to 20 carbon atoms or is absent
  $R_4$ is H or $CH_2O$—$R_3$; and $R_1$, $R_2$ and $R_3$ are the same or different and are either hydrogen, methyl, ethyl, hydroxyl or an acyl group derived from a fatty acid having a carbon chain of 3 to 24 carbon atoms saturated or unsaturated, with the proviso that at least one of $R_1$, $R_2$ and $R_3$ is an acyl group derived from a fatty acid.

In a fourth aspect the present invention consists in a compound for use in introducing nucleic acid into a cell, the compound having the formula:

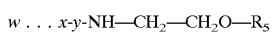

in which:
  w is a nucleic acid
  x is a peptide or amino acid
  y is a linker having a chain length equivalent to 1 to 20 carbon atoms or is absent
  $R_5$ is an acyl group derived from a fatty acid having a carbon chain of 3 to 24 carbon atoms saturated or unsaturated.

In a preferred form of each of the aspects of the present invention y is present.

In a preferred embodiment of the present invention the nucleic acid is DNA, RNA or oligonucleotides of either DNA or RNA, modified oligonucleotides or a combination of these. The nucleic acid may also bear chemical additives such as fluorescein (FITC), cholesterol, biotin or radiolabel.

The method of the present invention may be used for the delivery of nucleic acids including DNA, RNA, oligonucleotides of either DNA or RNA, modified oligonucleotides or a combination of these, to eucaryotic cells including established cell lines of animal or plant origin, primary cell lines of animal or plant origin, whole animals and plants whether applied systemically or topically or by aerosol. In this regard reference is made to EPO424688, the disclosure of which is incorporated herein by reference. The nucleic acid may also bear chemical additives such as fluorescein (FITC), cholesterol, biotin or radiolabel.

The method of the present invention is generally envisaged to involve the application of the compound in an essentially aqueous mixture to the surface of the cells of interest. However, in the case of whole organisms it may be necessary to apply the compound in an essentially non-aqueous form, by localised or systemic injection, topically or by inhalation.

The description of this invention includes the addition of labelling compounds such as fluorescein (FITC) or biotin to the peptide for visualisation and tracking in cells and organisms. Labelled compounds would be administered to cells by any of the routes or methods described above.

The peptide may be of any length and may include functional domains such as nuclear localisation signals and/or nucleic acid binding domains. Such functional domains may be included in tandem, or on a bifurcating structure such as may be constructed using lysine. Typically, the peptide will possess an overall positive charge to attract and hold the nucleic acid by association, for example, a peptide of one or more lysine residues. The peptide may, however, be constructed to carry an overall neutral charge if this is advantageous for different forms of delivery eg. for systemic delivery in vivo.

The linker may be any of a number of molecules well known in the art. It is, however, presently preferred that the linker is an amino acid or peptide, for example alanine, leucine, glycine, phenylalanine, lysine or homo or mixed polymers thereof. The linker may also include atypical amino acids, thereby allowing extension of the linker length beyond that of a standard amino acid. In this regard it is particularly preferred that the linker is amino butyric, amino caproic or amino caprylic acid.

In yet a further preferred embodiment of the present invention $R_1$, $R_2$ and $R_3$ are the same, and are preferably acyl derivatives of fatty acids including the group consisting of palmitate, myristate, laurate, caproate, oleate and cholesterol and particularly either laurate or myristate.

In the present applicant's Australian patent application No. 649242 there is disclosed a method of linking amino acids or peptides to 1 to 3 acyl derivatives of fatty acids via a tromethamine or ethanolamine derivative. Using this method a wide range of peptide/acyl derivatives of fatty acid conjugates having 1 to 3 acyl derivatives of fatty acid residues can be formed. It is by using the method disclosed in this application that the lead compound trilysine alanine tris tripalmitate (K3ATP3) can be formed. The disclosure of this application is incorporated herein by reference.

The nucleic acid ("w" of compound) may be associated with the remainder of the compound using positively charged amino acids for example lysine, arginine, ornithine ect at position "x" of the compound. Particularly preferred groups are monolysine, dilysine, trilysine, tetralysine or pentalysine groups. Alternatively the nucleic acid may be covalently linked to the peptide or amino acid "x". Further the linker group alanine may be substituted by, for example, leucine, glycine, phenylalanine or α-BOC (ε-free) lysine groups and the number of acyl derivatives of fatty acids may be varied from 1 to 3. It should also be noted that where it is desired to use one acyl derivative of fatty acids the tris may be replaced with ethanol amine.

It is also believed that formulation into liposomes by standard methods with a lipid such as dioleoyl phosphatidyl ethanolamine (DOPE), DOPC (DOP choline) or cholesterol may increase the capacity of the invention to facilitate delivery of compounds into cells. This is particularly likely where there are 2 fatty acyl derivatives. Methods for formulating liposomes are described, for example, in Feigner, P. L. et al 1987 PNAS 84 pp 7413–7417 and Yago, K et al 1993 Biochem and Biophys. Res. Comm. 196(3) pp 1042–1048. It has also been shown that the simple addition of DOPE to solutions of compounds can significantly enhance their activity (experiment 4 below, VerafectinG2±DOPE). Similarly other modifications of transfection conditions, with additives such as salts can enhance transfection. Changes in ionic strength and the presence of alkaline earth cations have been described as altering transfection efficiency (Loeffler and Behr, Methods in Enzymology 1993, H, 599–654).

A major application of this invention would be as a gene therapy delivery agent. The relatively efficient transfer of genes into cells observed so far, coupled with the low toxicity (particularly when compared to commercially available agents) makes the invention an ideal series of compounds for therapeutic use. Further information regarding gene therapy may be found in Nabel et al, 1993 PNAS 90 pp 11307–11311, the disclosure of which is incorporated herein by reference.

In order that the nature of the present invention may be more clearly understood, preferred forms thereof will now be described with reference to the following examples and Figures in which:

Cytotoxicity was assayed using a standard MTT (3-[4,5, Dimethylthiazol-2-yl]2,5-diphenyltetrazolium bromide; Thiazolyl blue) assay. Verafectin is K3ATP3 and the concentration is shown in $\mu$M, DMSO was used at an equivalent concentration to that of the diluent for Verafectin.
  a. Cell death results in a decrease in OD
  b. Cell survival in the presence of diluted DMSO alone was taken as 100% and survival in the presence of Verafectin adjusted accordingly.

Figure 2A:
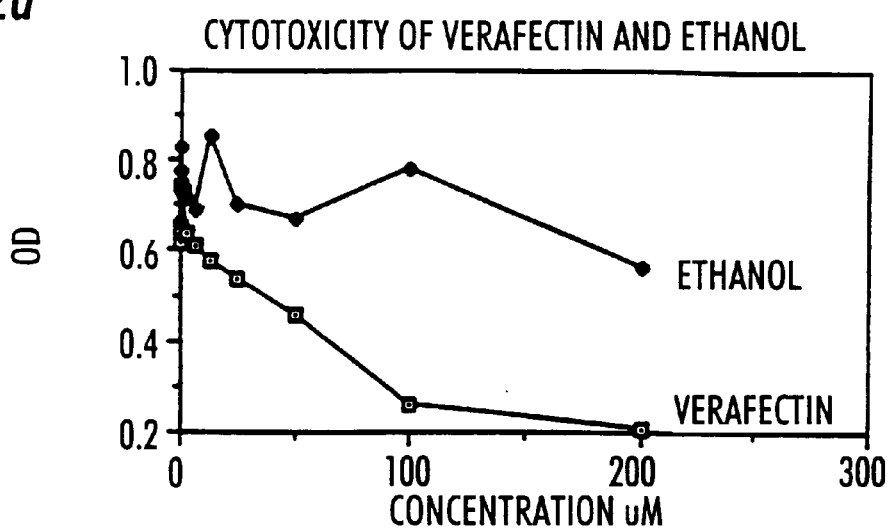
Figure 2B:
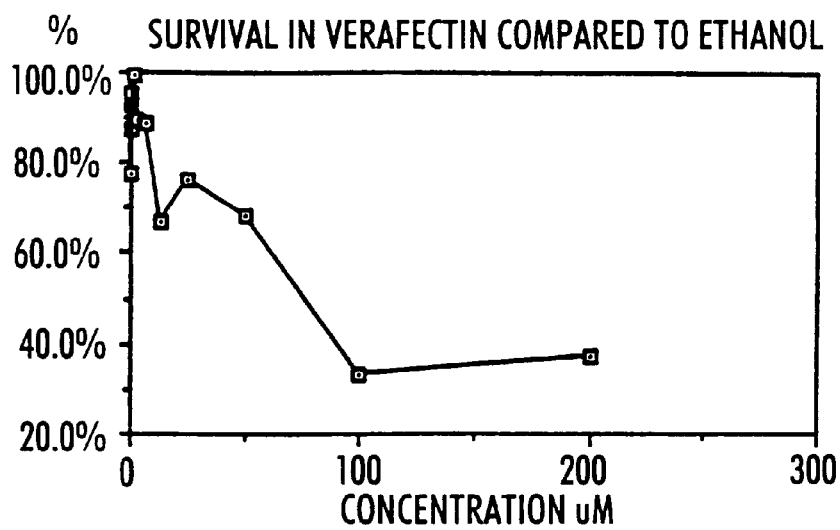

FIG. 2a shows cytotoxicity of Verafectin and ethanol and 2b shows % survival in Verafectin compared to ethanol.

Cytotoxicity was assayed using a standard MTT (3-[4,5, Dimethylthiazol-2-yl]2,5-diphenyltetrazolium bromide; Thiazolyl blue) assay. Verafectin (K3ATP3) was dissolved in 100% warm ethanol at 10 mg/ml and subsequently diluted in water to the concentrations shown in $\mu$M.
  a. Ethanol was diluted in parallel and tested for cytotoxicity at the same concentrations as the diluent for Verafectin.
  b. Cell survival in the presence of diluted ethanol alone was taken as 100% and survival in the presence of Verafectin adjusted accordingly.

Figure 3:
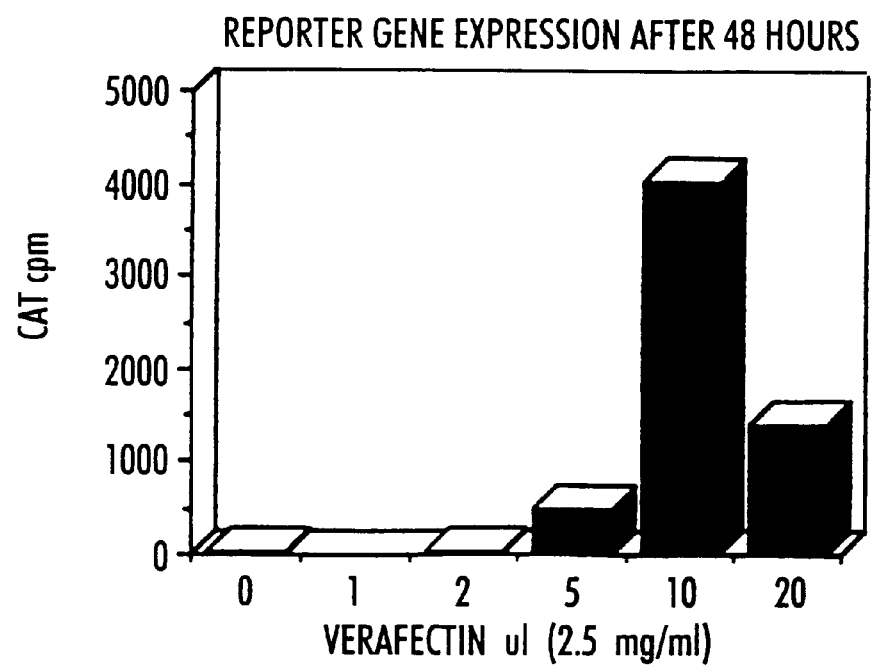

FIG. 3 shows CAT expression 48 hours after transfection of pSVLCAT mediated by Verafectin.

The amount of Verafectin shown in $\mu$M was mixed with 1 $\mu$g of pSVLCAT before overlaying on cells for transfection. Results shown are the levels of CAT expression measured from 50 $\mu$l cell culture medium 48 hours after transfection.

Figure 4:
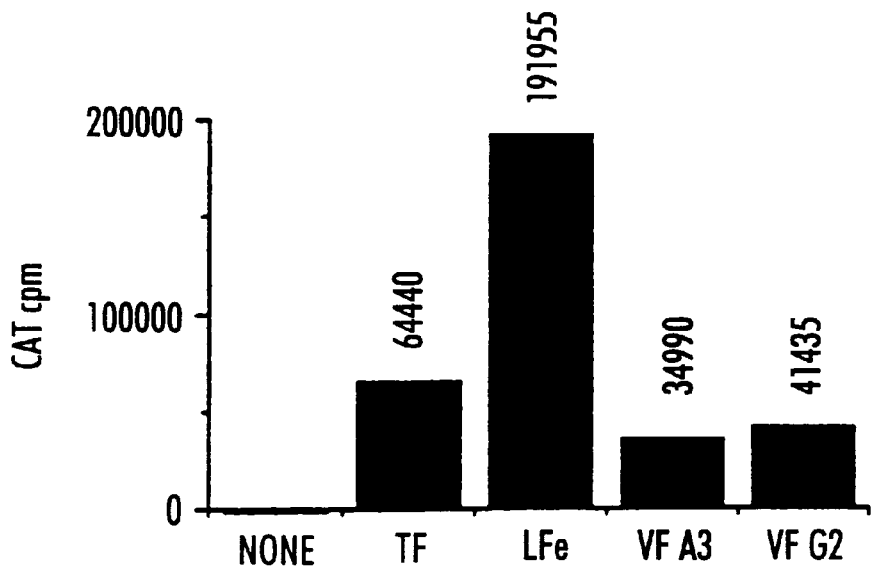

FIG. 4 shows CAT expression assayed 48 hours after transfection of CHO cells mediated by test agents.

Results shown are from the concentration of transfection agent giving the highest level of transfection in the experiment. This was 5 $\mu$l in each case. CAT assays were done by the method of Neuman J. R., Morency, C. A. and Russian, K. O. (1987) Biotechniques 5, p444–447. None: no transfection agent, TF; Transfectam (Promega), Lfe; Lipofectamine (BRL), VF A3: K3ATP3, VF G2; K3GTP2.

Figure 5:
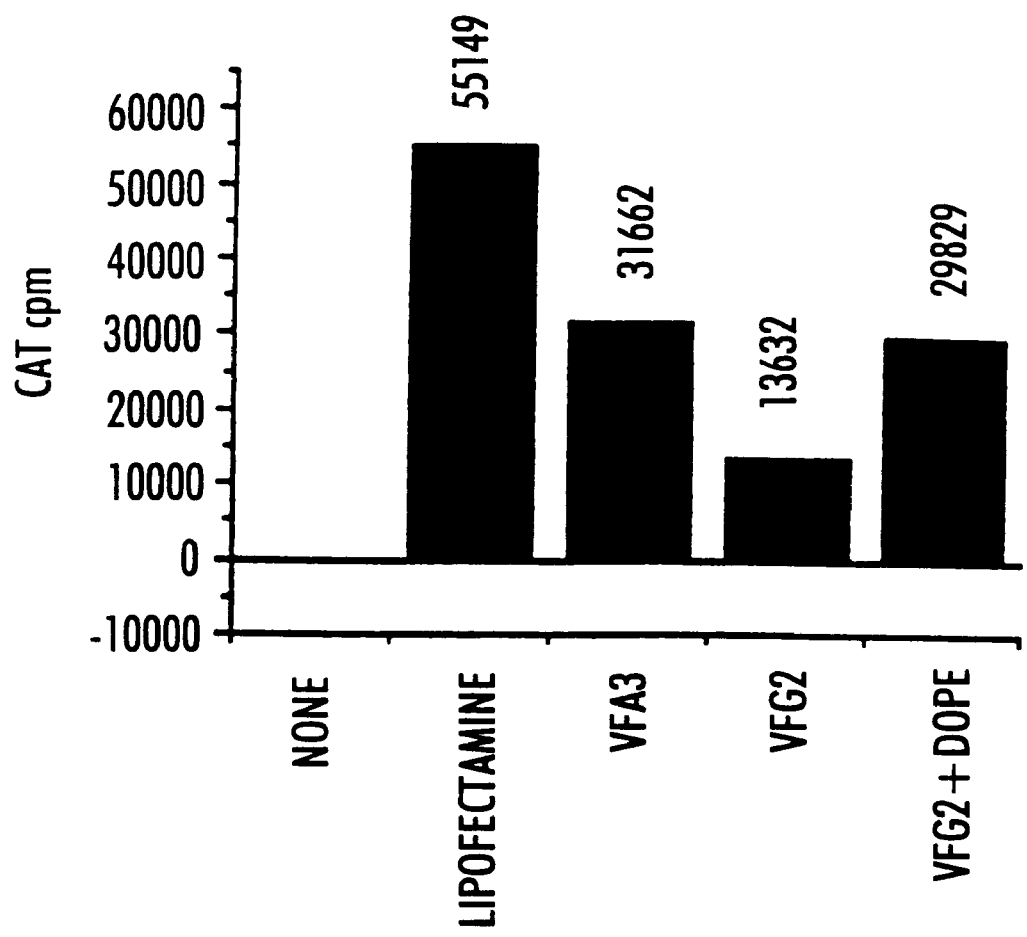

FIG. 5 shows CAT expression assayed 48 hours after transfection of Cos 1 cells, mediated by test agents.

Results shown are from the concentration of transfection agent giving the highest level of transfection. None; no agent, VF A3; K3ATP3, VF G2; K3GTP2, VF G2+DOPE; K3GTP2+DOPE.

FIG. 6 shows relative Cytotoxicity of transfection agents Legend
  a. (CHO cells) Cell viability following transfection with different agents at time of cell harvest for CAT assay. None; No transfection reagent, TF; Transfectam, Lfe; Lipofectamine, VF G2; Verafectin G2 all at 5 $\mu$l. High OD indicates high cell survival.
  b. (Cos 1 cells) Cell viability as for FIG $a$. VF A3; Verafectin A3 9 $\mu$l, Lfe 5 $\mu$l. Assays in this experiment were done in 35 mm dishes.

Figure 7A:
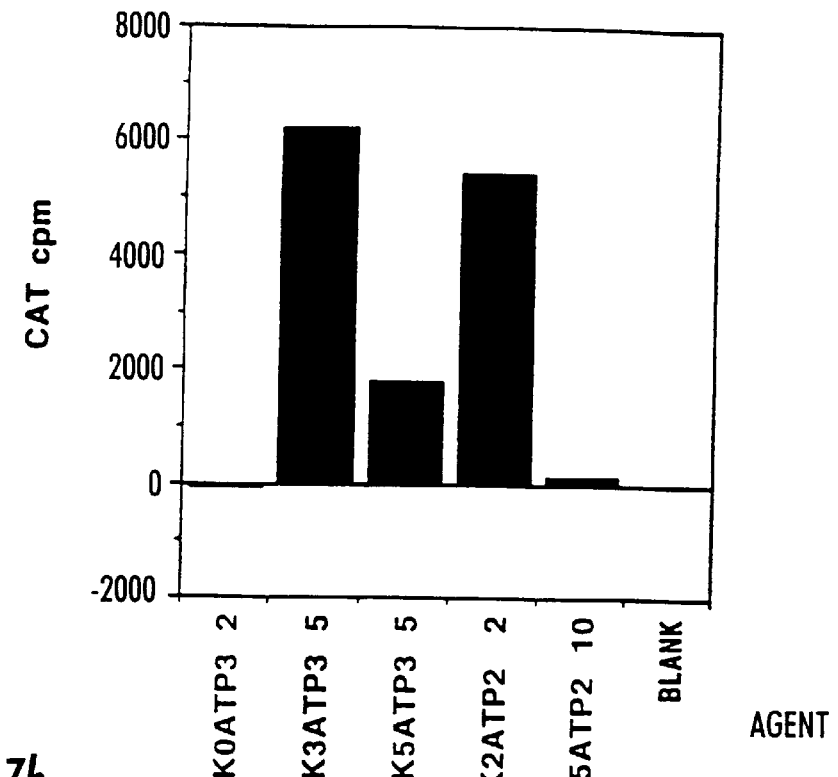
Figure 7B:
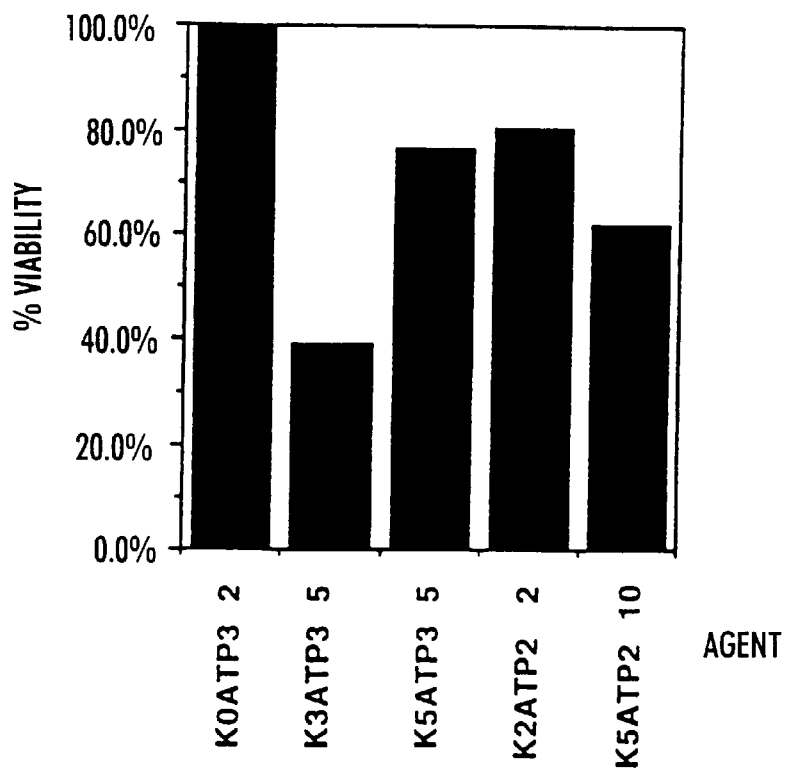

FIGS. 7a and 7b shows results of "x" peptide experiment "a"

Figure 8:
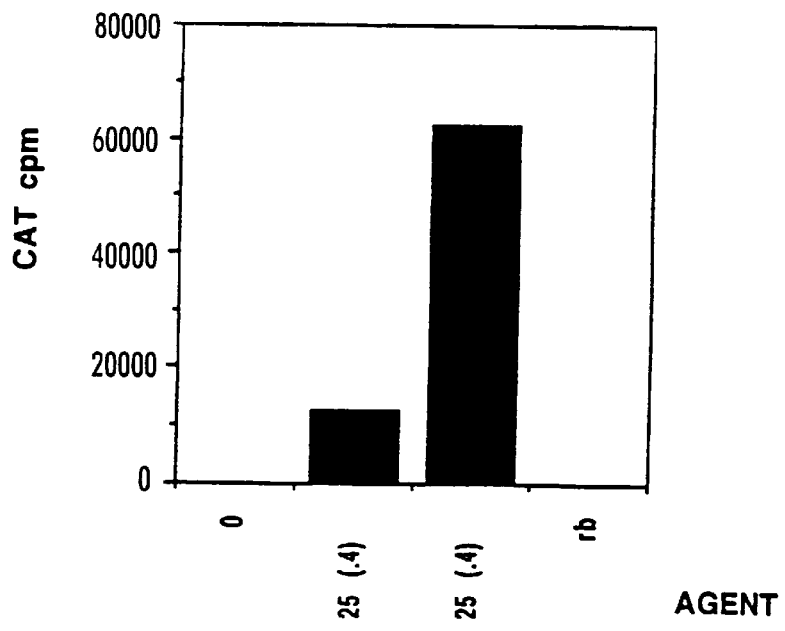

FIG. 8 shows results of "x" peptide experiment "b"

Figure 9:
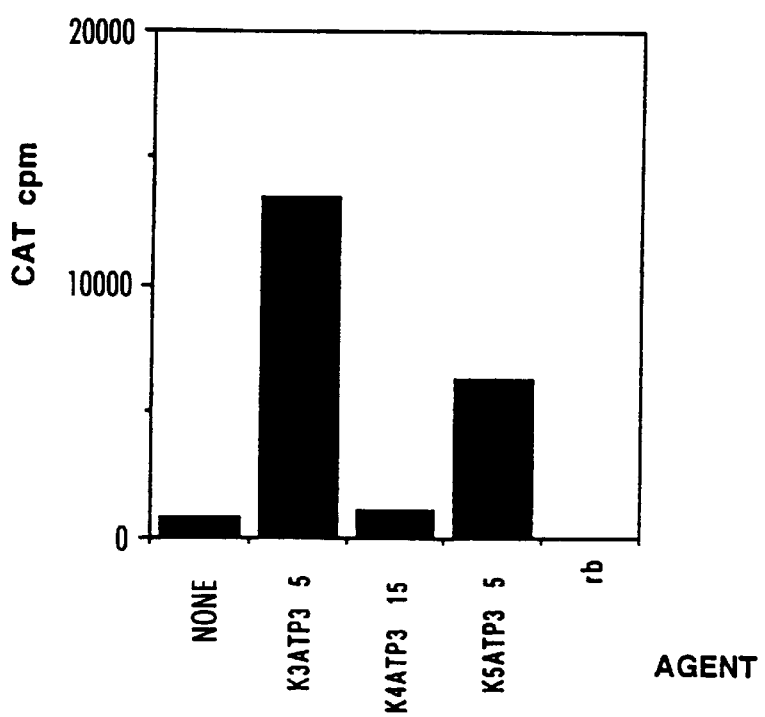

FIG. 9 shows results from "x" peptide experiment "c"

(LEGEND—FIGS. 7, 8 and 9; none; no agent used with plasmid DNA, rb/blank; reagent blank, number following description of compound indicates no. μl of 2 mM stock (diluted with water). 7b: 100% cell survival was taken from dishes which were "mock transfected" with no DNA or transfection agent. 0% viability was assayed in the absence of cells. Viability was assessed using the dye alamar blue.)

Figure 10A:
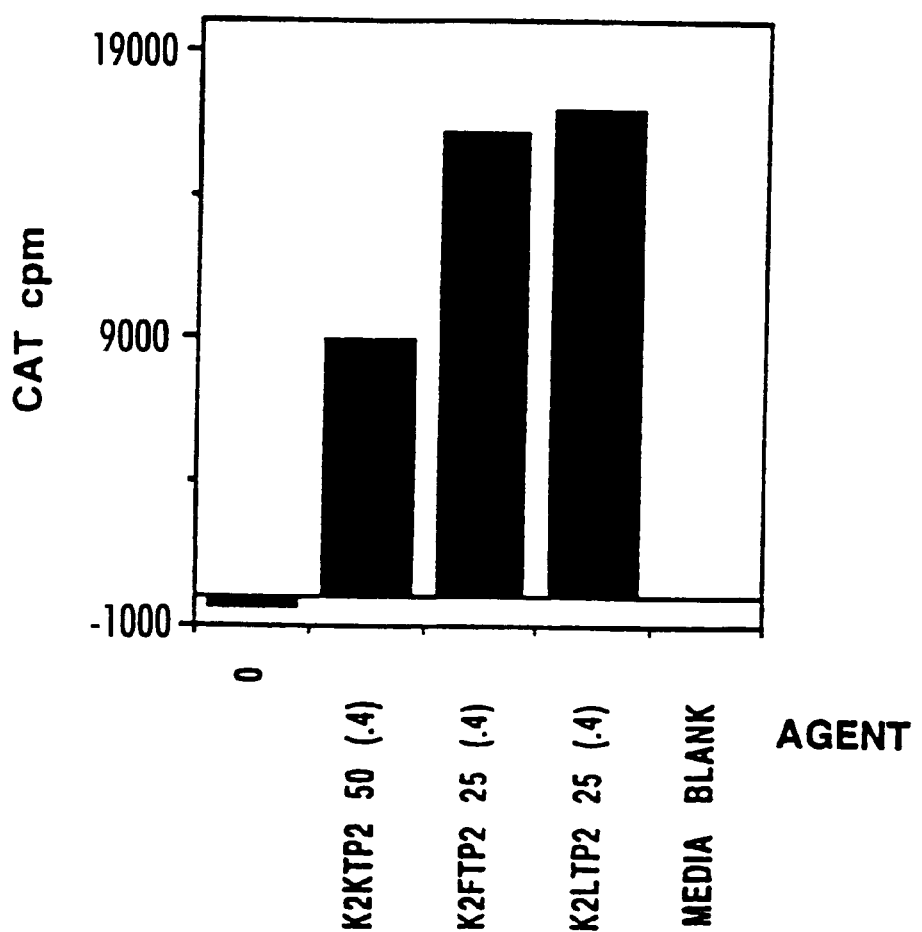
Figure 10B:
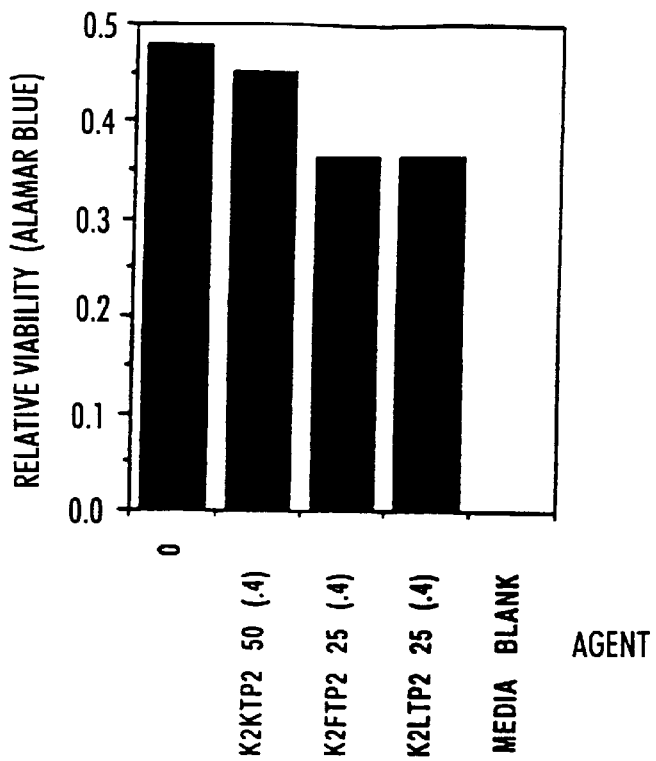

FIGS. 10a and 10b shows results from "y" linker experiment "a"

Figure 11:
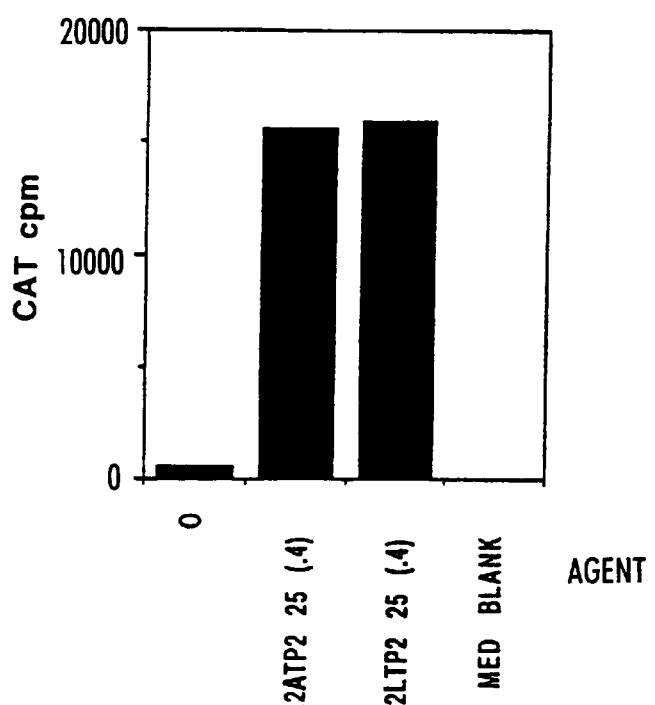

FIG. 11 shows results from "y" linker experiment "b"

Figure 12:
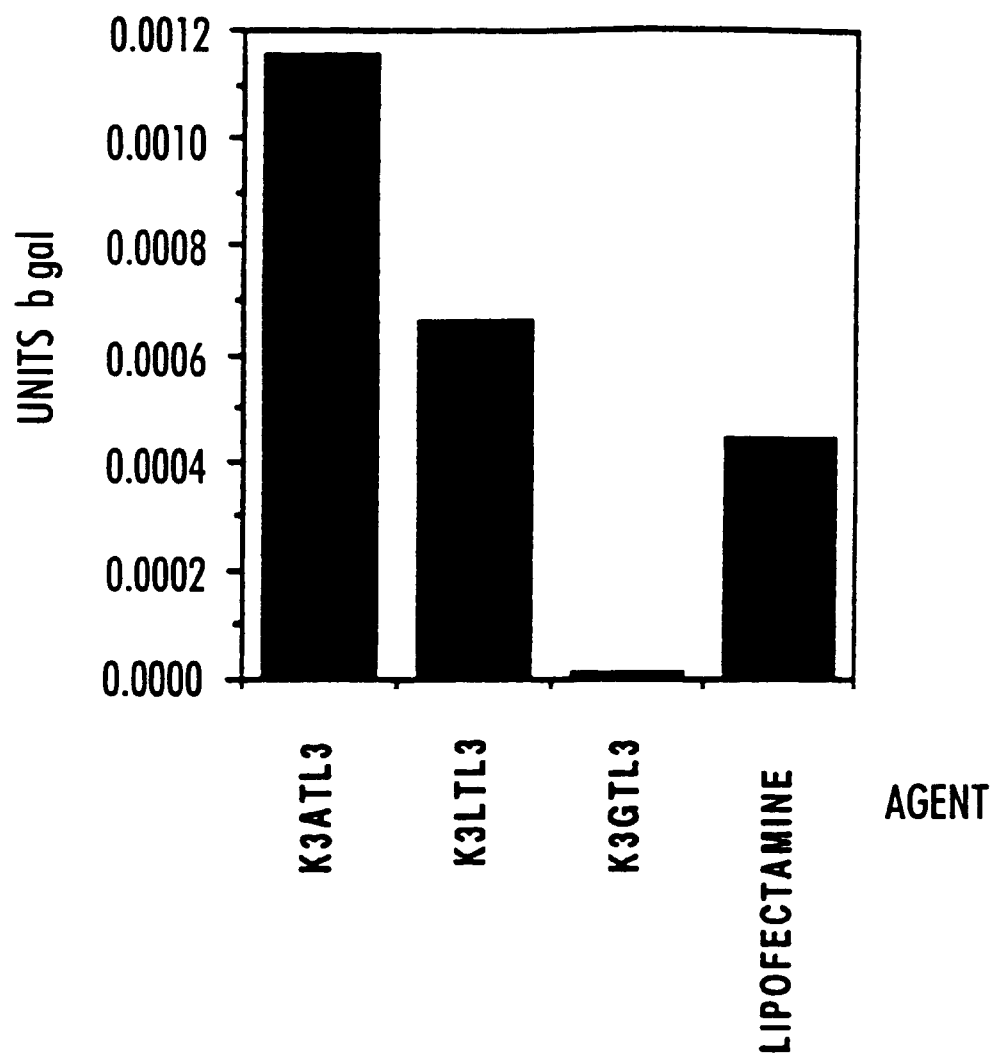

FIG. 12 shows results from "y" linker experiment "c"

(LEGEND—FIGS. 10a, 10b, 11, 12; agent; test compound from 2 mM stock unless otherwise specified. (0.4); agent stock at 0.4 mM. 0: no agent. DNA alone under standard transfection conditions. Media blank: media alone in CAT assay. relative viability (alamar blue): Measure of $OD_{570-595}$ of the culture medium with alamar blue added for a period of incubation at 37° C.)

Figure 13A:
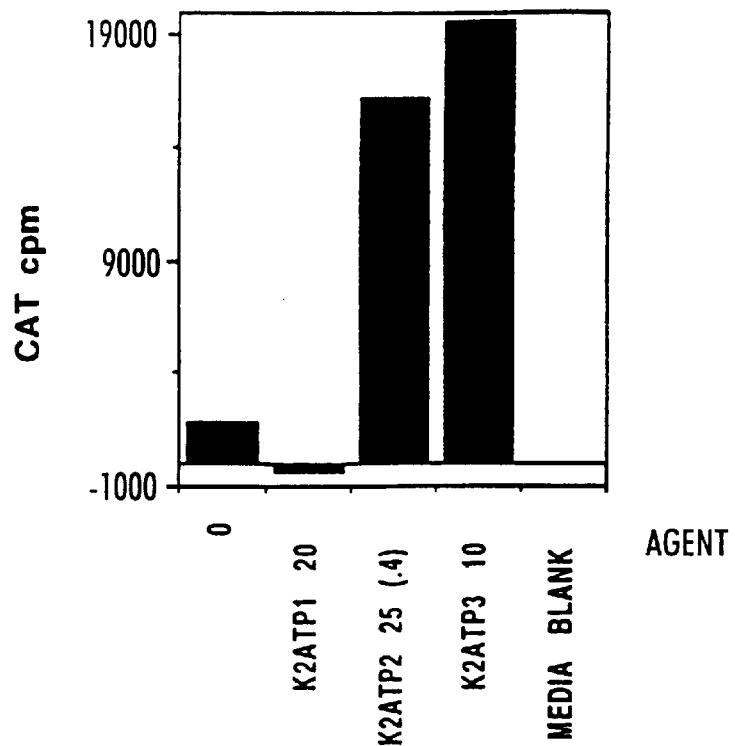
Figure 13B:
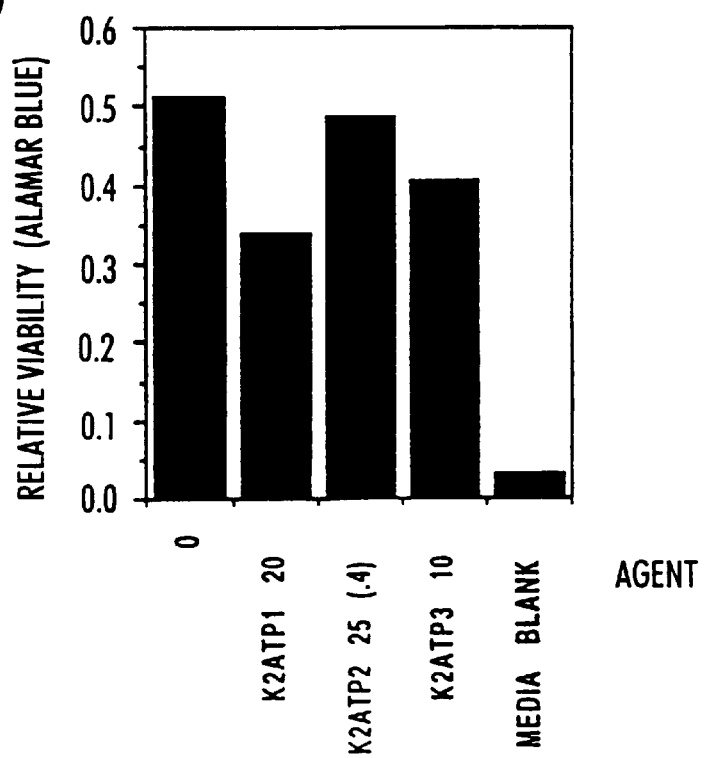

FIGS. 13a and 13b shows results from R1–R4 derivative experiment "a".

(Legend: as for Legend FIGS. 10a, 10b, 11, 12)

Figure 14A:
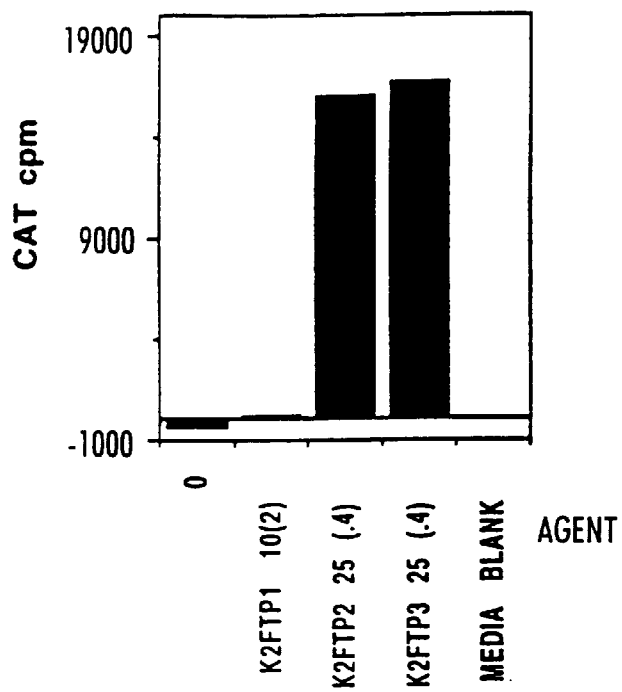
Figure 14B:
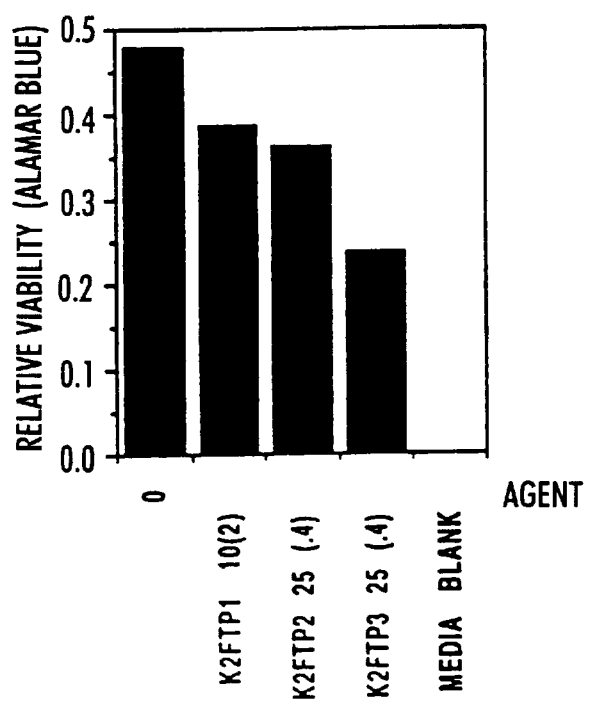

FIGS. 14a and 14b shows results from R1–R4 derivatives experiment "b"

(Legend: as for Legend FIGS. 10a, 10b, 11, 12)

Figure 15A:
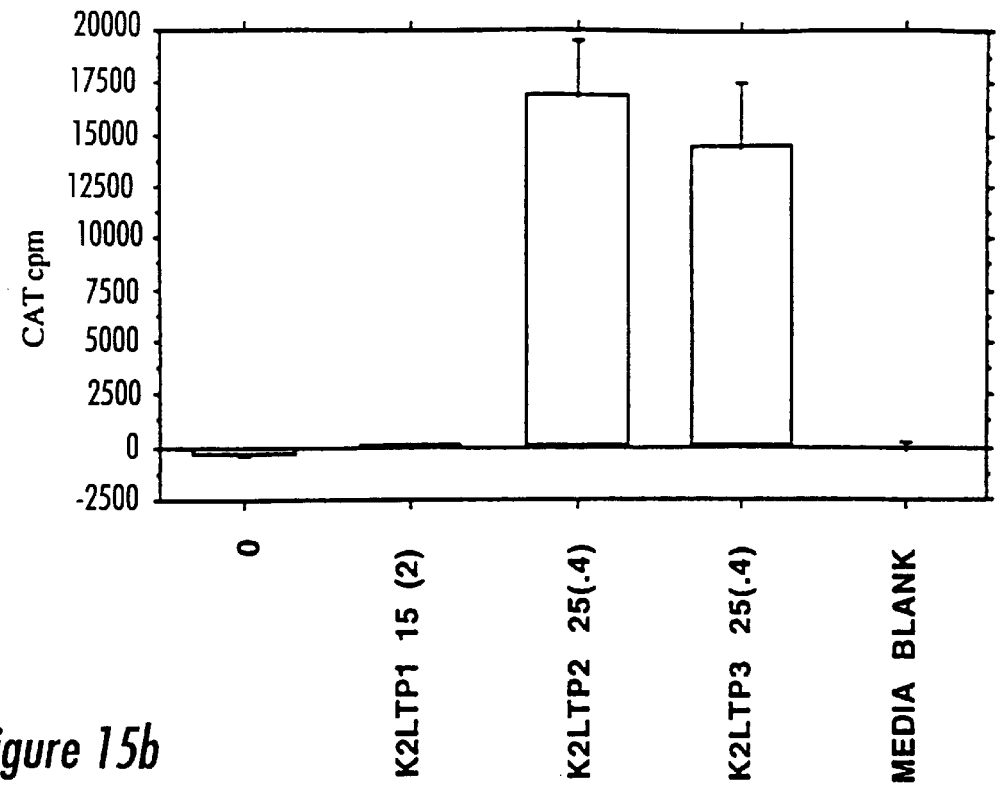
Figure 15B:
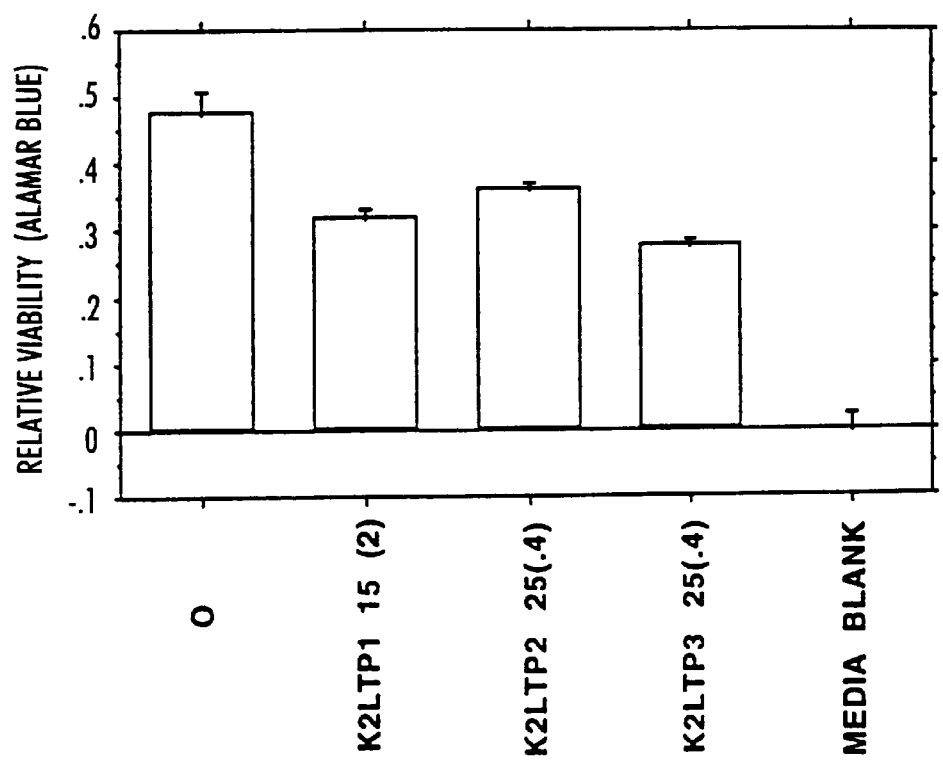

FIGS. 15a and 15b shows results from R1–R4 experiment "c"

(Legend: as for Legend FIGS. 10a, 10b, 11, 12. Standard Deviation is shown.)

Figure 16A:
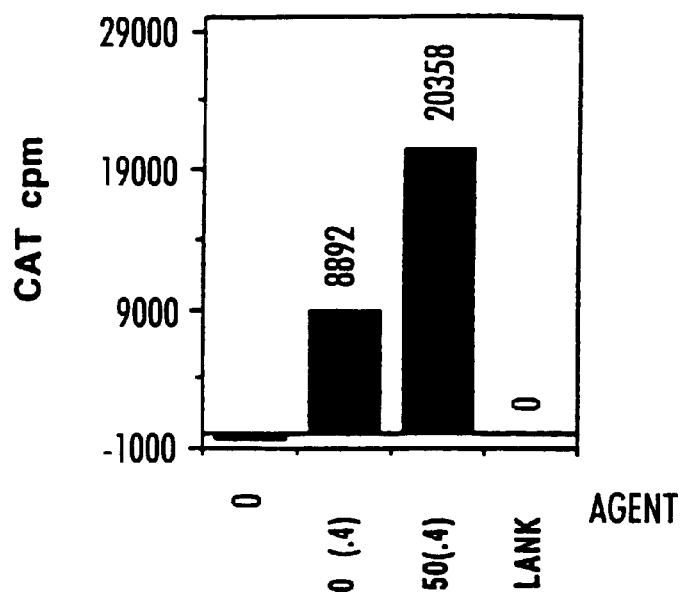
Figure 16B:
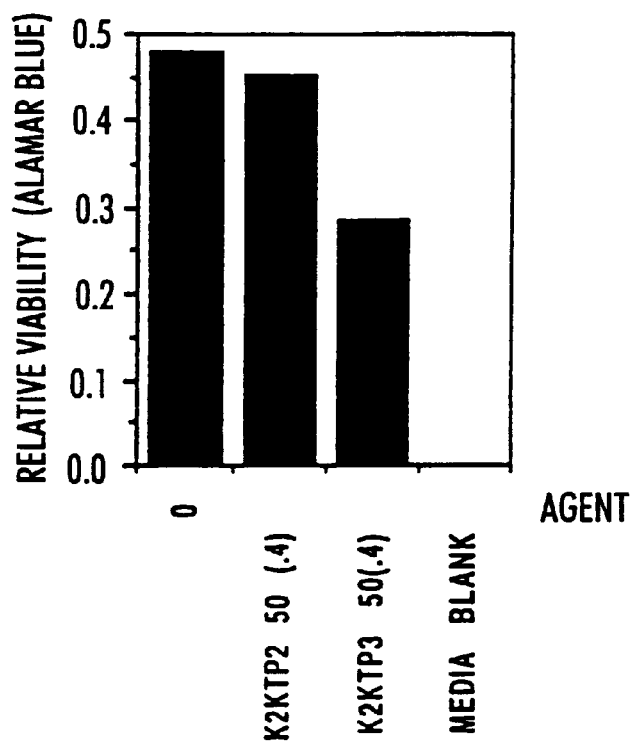

FIGS. 16a and 16b shows results from R1–R4 derivatives experiment "d"

Figure 17A:
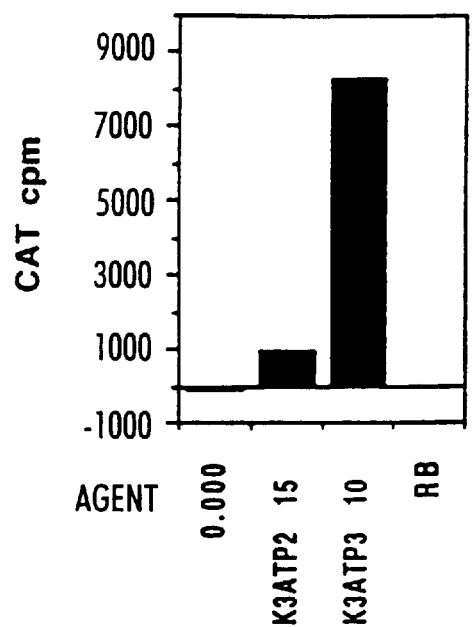
Figure 17B:
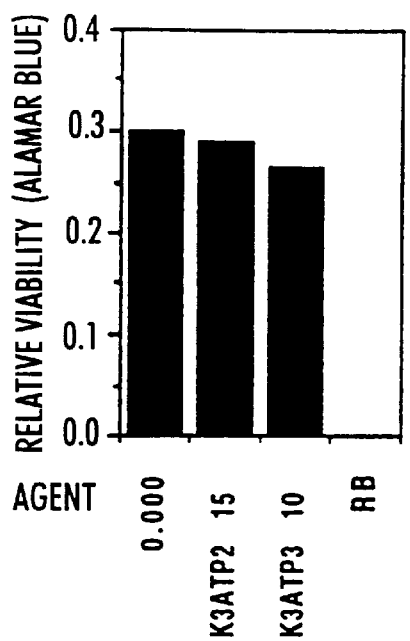

FIGS. 17a and 17b shows results of R1–R4 derivatives experiment "e"

Figure 18A:
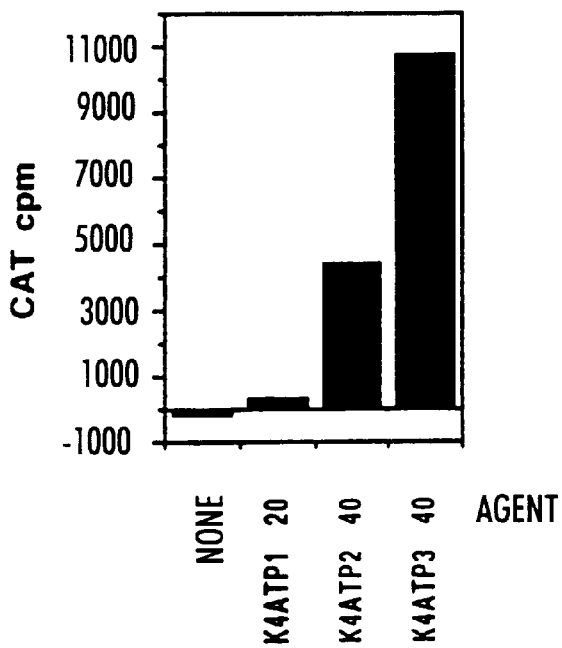
Figure 18B:
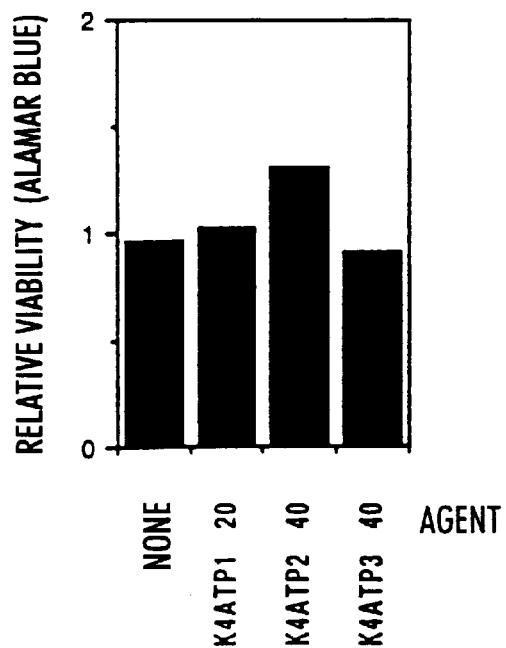

FIGS. 18a and 18b shows results of R1–R4 derivatives experiment "g" Cos 1 cells were transfected according to the standard assay in 60 mm dishes. 50 μl 48 hr culture supernatant was incubated for 5 hours at 37° C. for the CAT assay.

Figure 19A:
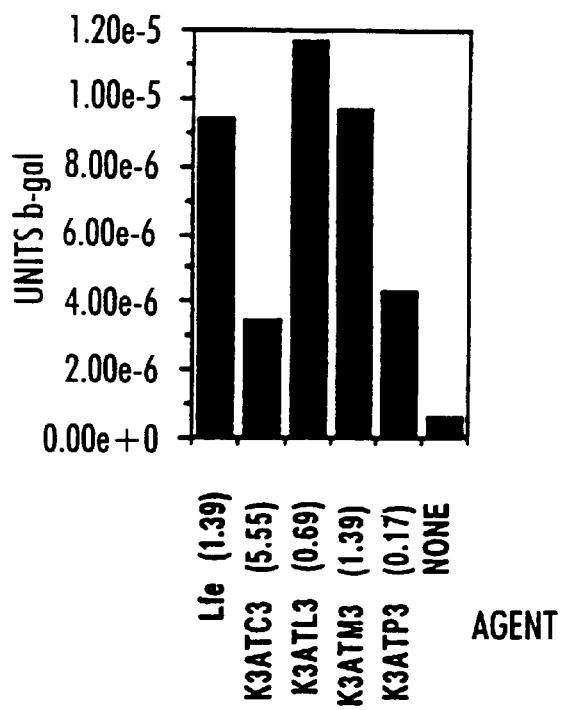
Figure 19B:
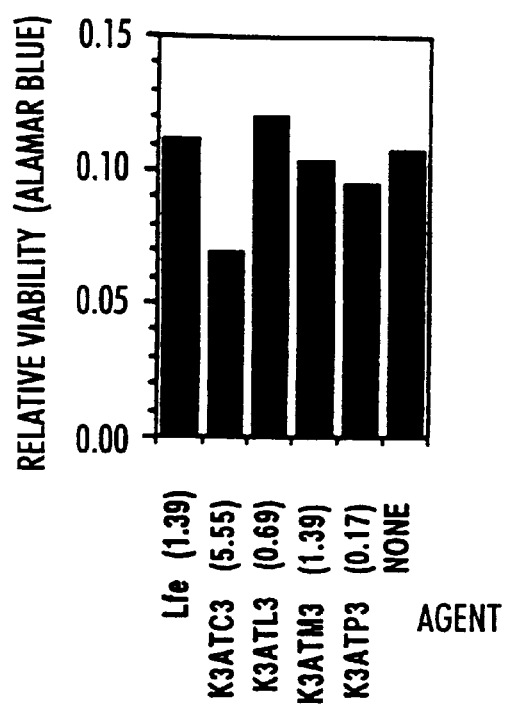

FIGS. 19a and 19b shows the results of R1–R4, C10–C16 experiment "b". Hela cells.

(Legend—FIGS. 19a and 19b; Lfe; Lipofectamine, (1.39) ratio of [lipid]/[DNA] at which optimal transfection occurred, NONE; no agent but DNA included in transfection. Cytotoxicity was determined with Alamar blue.)

Figure 20A:
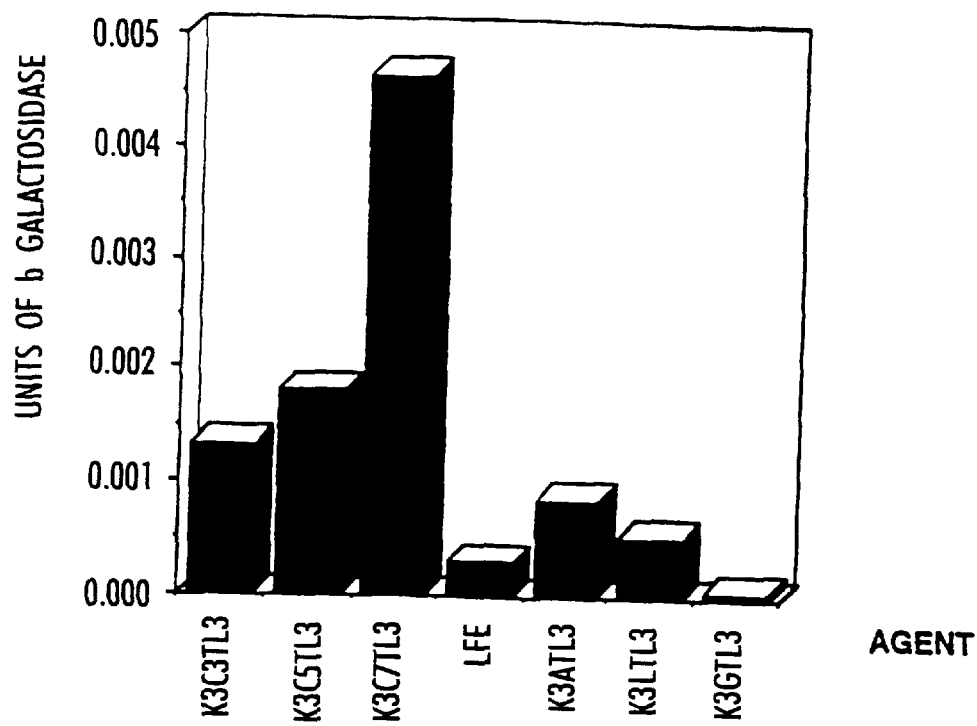
Figure 20B:
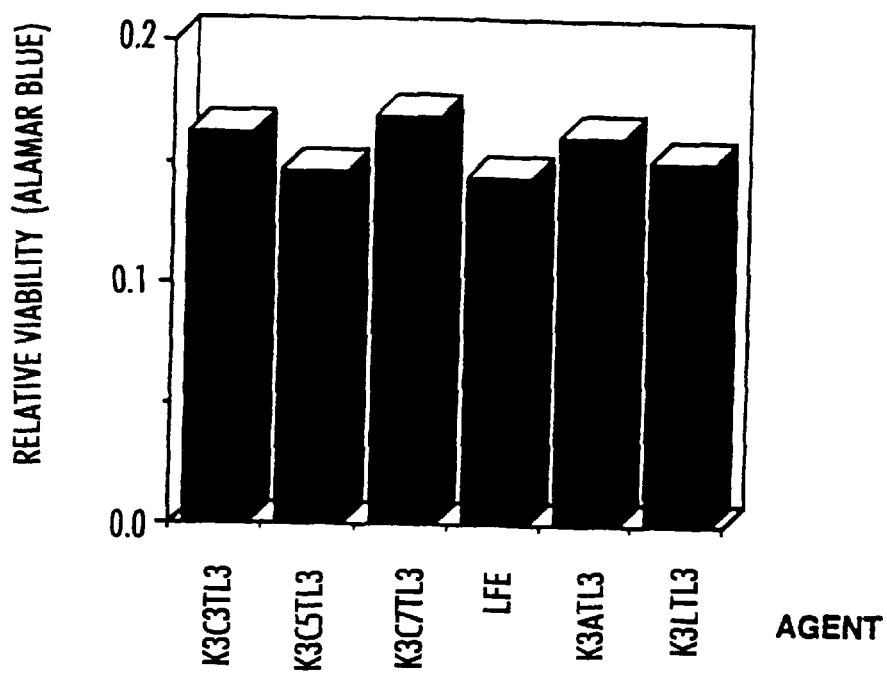

FIGS. 20a and 20b shows results from "y" linker non-standard amino acids experiment "1".

(Legend; LFE; Lipofectamine. Levels of gene expression are shown in "a" as units of β-galactosidase. Relative viability was assayed in "b" using the dye "alamar blue" and is shown as the optical density measured after a period of incubation in the presence of the dye. High OD indicates high cell survival.)

Figure 21A:
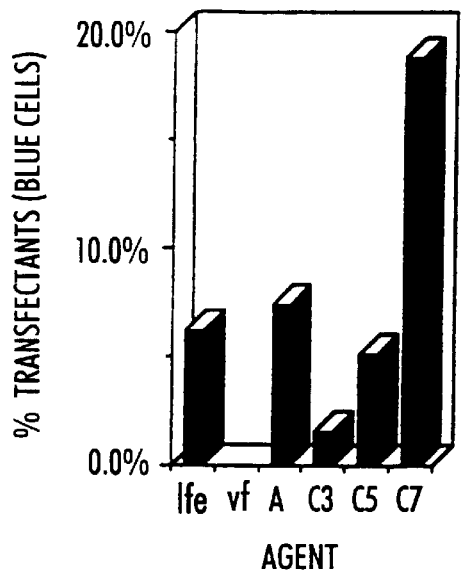
Figure 21B:
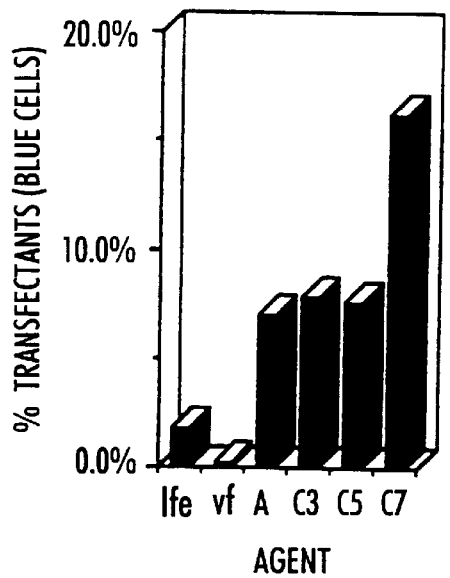

FIGS. 21a and 21b shows results from "y" linker non-standard amino acids "experiment 2".

(Legend; lfe; Lipofectamine, vf; Verafectin A3, C3; K3C3TL3, C5; K3C5TL3, C7; K3C7TL3, % Transfectants was calculated from the number of blue staining cells over a number of fields compared to those cells not stained. a; CHO cells, b; Cos 1 cells.)

Figure 22A:
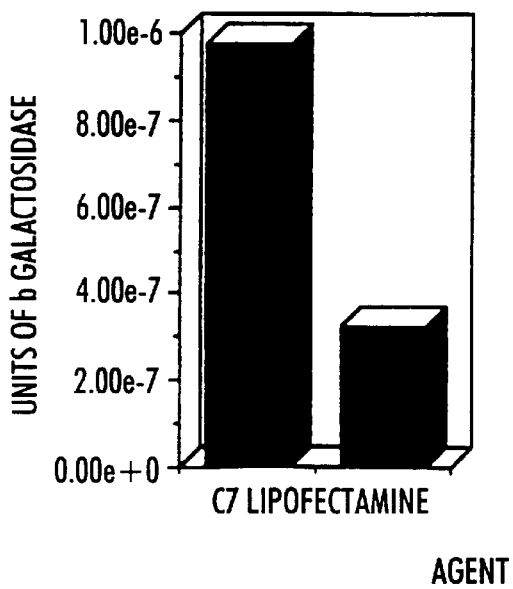
Figure 22B:
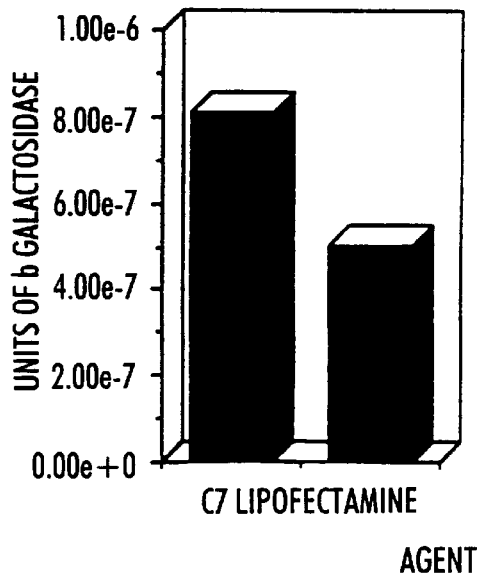

FIGS. 22a and 22b shows results from "y" linker non-standard amino acids on PC3 and Jurkat cell lines.

Figure 23A:
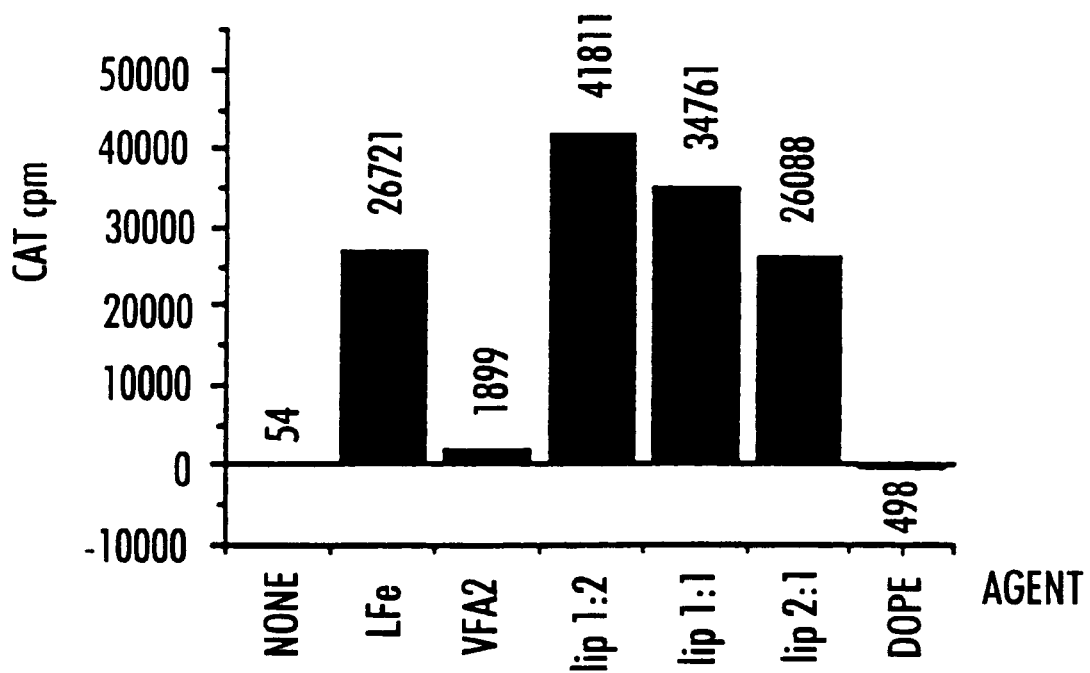

FIG. 23a shows results of "formulation" experiment "A". CAT expression from CHO cells transfected using different liposome formulations, constituents and Lipofectamine (Lfe). Results of a representative experiment are shown.

Figure 23B:
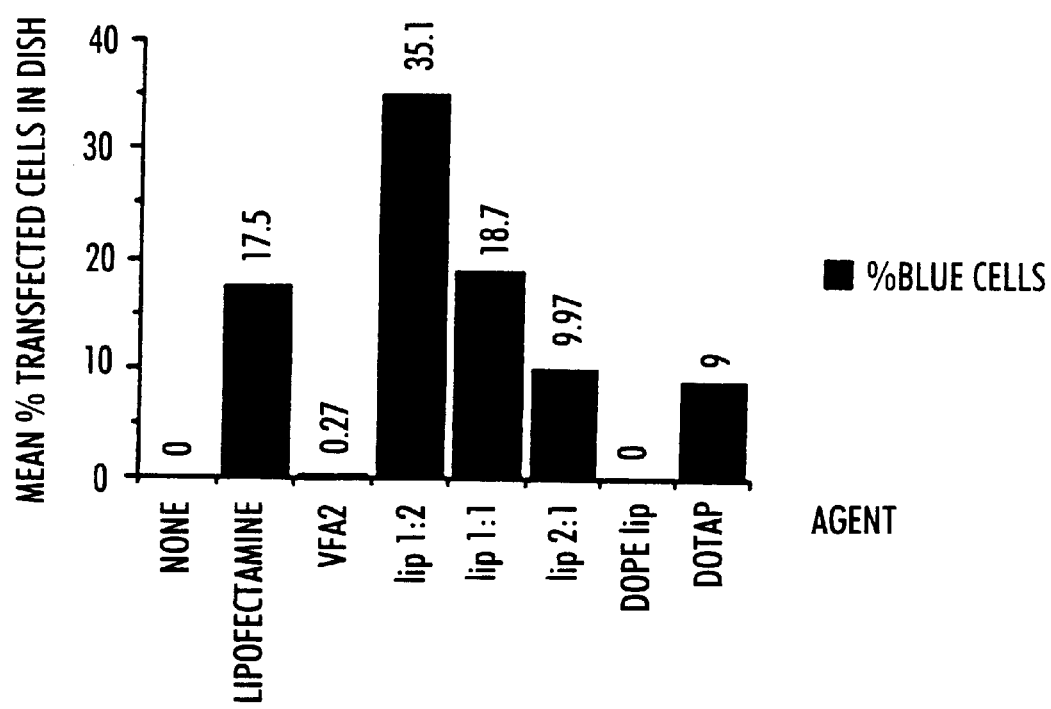

FIG. 23b shows results of "formulation" experiment "b". Percentage of cells transfected using liposome formulations, constituent agents and commercial preparations. VF A2; K3ATP2. Liposomes were formulated using VF A2 and DOPE at the designated ratio of VF A2: DOPE. Results shown are of a single experiment.

Figure 24:
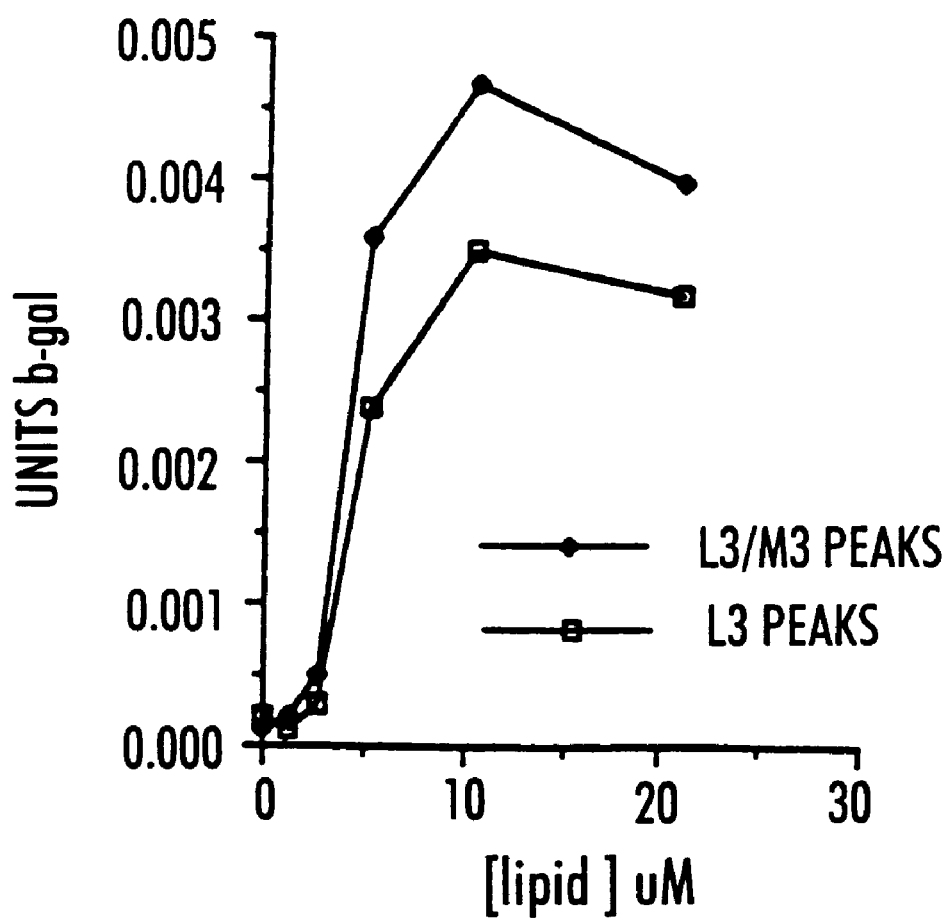

FIG. 24 shows results of "Unformulated mixtures" experiment "2"

(Legend; Transfection efficiency is gauged as the level of β-gal units expressed after 48 hours. L3: K3ATL3, M3; K3ATM3. Peak indicates the combination of lipopeptide and DNA giving the highest reading. [lipid] indicates the concentration of total lipopeptide used.)

EXAMPLES

Chemistry

Abbreviation used

α-BOC(ε-Z-Lys)=α-Butyloxycarbonyl-ε-carbobenzoxy-Lysine

AEP=Alanine-Ethanolamine-palmitate

ATP1=Alanine-Tris-monopalmitate

ATP2=Alanine-Tris-dipalmitate

ATP3=Alanine-Tris-tripalmitate $CDCl_3$=Chloroform-d

DCCD=Dicyclohexylcarbodiimide,

DCM=Dichloromethane,

DIEA=Diisopropylethylamine,

DMAP=Dimethylaminopyridine,

DMF=Dimethylformamide,

DMSO-$D_6$=Dimethylsulfoxide-d6

DSC=Disuccinimidylcarbonate,

FATP1=Fluorescein Alanine-Tris-monopalmitate

FATP2=Fluorescein Alanine-Tris-dipalmitate

FATP3=Fluorescein Alanine-Tris-tripalmitate

FITC=Fluorescein isothiocyanate (isomer I)

HOSU=Hydroxysuccinimide,

TEA=Triethylamine

TFA=Trifluoroacetic acid,

THF=tetrahydrofuran,

Tris=2-amino-2-hydroxy-methyl-1,3 propanediol.

Z=N-carbobenzoxy

MATERIALS AND METHODS

α-BOC(ε-Z-Lys) was purchased from Peptide Institute, Inc. (Osaka, Japan) and DSC was purchased from Tokyo Kasei Kogyo Co. (Tokyo, Japan). All the amino acids were L-configuration and were purchased from the Sigma Chemical Company (St. Louis, Mo.) unless otherwise mentioned. All solvents were of analytical grade and were used as purchased.

THIN LAYER CHROMATOGRAPHY (TLC)

Performed on Alufolein Silica gel 60 $F_{254}$ plates (Merck) in the following solvent systems; $R_f^1$, chloroform/ methanol/ acetic acid: 95/5/3; $R_f^2$ chloroform/ methanol/ triethylamine: 95/7/3:

HIGH PERFORMANCE LIQUID CHROMATOGRAPHY (HPLC)

Analytical HPLC was carried out on Millipore Waters HPLC equipment (Waters Chromatography Division of Millipore, Milford, Mass.), comprising of a 6000A series solvent delivery system with an automated gradient controller and Model 746 Data Module, The chromatography was carried out with a NOVAPAK™ $C_{18}$ reverse phase column (100×8 mm). The peptides and the peptide-tris conjugates were analysed on a linear gradient elution from 24 to 80% acetonitrile with 0.1% TFA within 5 min at a flow rate of 2 ml/min (System A). Detection was carried out at 260 nm using a Waters Lambda Max 480; ($R_t^A$). The lipopeptide conjugates were analysed on a $C_{18}$ column with a linear gradient from 50% water, 50% acetonitrile with 0.1% TFA to 50% acetonitrile, 50% THF with 0.1% TFA within 5 min at a flow rate of 2 ml/min (System B); ($R_t^B$). Separation of fluorescein-labelled compounds was carried out on a Prep-Pak® C4 Semipreparative Reverse Phase column (25×10) at a flowrate of 6 ml/min.

PREPARATIVE HPLC

Separations were carried out on a Millipore Waters DeltaPrep 4000 HPLC using a PrePak $C_4$ reverse phase column (100×40 mm) eluted with a linear gradient with the same eluent buffer systems as mentioned above for the analytical HPLC at a flow rate of 20 ml/min.

NUCLEAR MAGNETIC RESONANCE (NMR)

NMR spectra were recorded with a 200 MHz Brucker spectrophotometer.

CHEMICAL SYNTHESIS

Preparation of ATP1, ATP2 and ATP3

These compounds were obtained by hydrogenation of Z-Ala-Tris-mono, di. and tripalmitates at 40 psi. pressure in a Parr hydrogenator in the presence of palladium on carbon (10%) in ethanol. The removal of the benzyloxycarbonyl group was monitored by HPLC (System B). After removing the catalyst by filtration and evaporation of solvents, ATP1, ATP2 and ATP3 were obtained in quantitative yields. The syntheses and purification of ZATP1, ZATP2, ZATP3 and the corresponding glycyl compounds are described in Whittaker, R. G., Hayes, P. J. and Bender, V. J., 1993), *Peptide Research*, 6, 125–128., and Whittaker R. W. U.S. Pat. No. 649,242, Amino acids, peptides or derivatives thereof coupled to fats.

Preparation of FATP1, FATP2 and FATP3.

To a solution of ATP1 (10 mg, 25 μmole) in DCM (500 μl) a solution of FITC (10 mg 25 μmole) in DMF (500 μl) was added with stirring. The apparent pH of the reaction was maintained at 9.0 by the addition of TEA and the reaction monitored by HPLC (System B). The formation of Fluorescein-Ala-Tris-palmitate was complete in 10 min and the product was purified by preparative HPLC to give the FATP1 product in chromatographically pure state, $R_t$: 7.08. The solvents were removed under reduced pressure and the FATP1 product lyophilised from tert. butanol.

FATP2 and FATP3 were synthesised in the same manner by reacting ATP2 (16.3 mg, 25 μmole) and ATP3 (22 mg, 25 μmole) in DCM (500 μl) with FITC (10 mg, 26 μmole) to give the chromatographically clean products $R_t$: 8.61 and 9.92 respectively.

Preparation of Fluorescein-labelled Alanine-Ethanolamine-Palmitate

Alanine-Ethanolamine-palmitate (AEP) was prepared by hydrogenation of Z-Ala-Ethanolamine-palmitate in a Parr hydrogenator in the presence of palladium on charcoal (10%) in ethanol. The removal of the benzyloxycarbonyl group was monitored by HPLC (System B). After removing the catalyst by filtration and evaporation of the solvent the title compound was obtained in quantitative yield.

Preparation of $(Lys)_n$ compounds

The synthesis and purification of Z-Ala-Ethanolamine and the corresponding palmitate are described in Whittaker, R. G., Hayes, P. J. and Bender, V. J., (1993), *Peptide Research*, 6, 125–128., and Whittaker R. G. U.S. Pat. No. 649,242 Aminio acids, peptides or derivatives thereof coupled to fats.

To a solution of AEP (20 mg, 54 μmole) in DMF (500 μl) FITC (22 mg, 56 μmole) was added with stirring and the apparent pH maintained at 9.0 by the addition of TEA. The reaction was complete in less then 20 min and the product purified by preparative HPLC to give the title compound in chromatographically pure state, $R_t$: 7.01.

The syntheses of the oligo-Lys compounds [(BOC(ε-Z-Lys)$_n$] were carried out by classical solution methods (1). The lipopeptides BOC(ε-Z-Lys)$_n$-X-Tris-palmitate were synthesised by coupling oligo-Lys and the palmitic acid through a linker amino acid (X)-Tris compound. The approach to the synthesis was to couple the BOC(ε-Z-Lys)$_n$-OH with an amino acid-Tris (2) by an activated ester method, and further coupling of the palmitic acid to this conjugate by the symmetrical anhydride method (1). The purity of the intermediate and the final product was checked by TLC, HPLC, and NMR.

1) Bodanszky, M. and Bodanszky, A. 1984. Principles of Peptide Synthesis, Springer-Verlag, Berlin.
2) Whittaker, R. G., Hayes, P. J., and Bender, V. J., 1993, A Gentle Method for Linking Tris to Amino Acids and Peptides, Peptide Research, 6, 3 (p. 125–128).

Typical synthesis examples are noted below

Step (I)

α-BOC(ε-Z-Lys)$_2$OH

α-BOC(ε-Z-Lys)OH, (9.9 g, 30 mmol) was dissolved in 100 ml DCM. HOSU (5.2 g, 45 mmol) and DIEA (9.0 g, 15 mmol) were added to the solution and it was cooled to 0° C. DCCD (6.2 g, 30 mmol) dissolved in 50 ml DCM was dropped into the reaction mixture. It was stirred at 0° C. for 1 h followed by room temperature overnight to obtain the activated ester (α-BOC(ε-Z-Lys)OSU in 86% yield by HPLC. The DCU (Dicyclohexylurea) precipitate was filtered off and α-amino (ε-Z-Lys)OH (7.56 g, 27 mmol) was added to the reaction mixture and it was stirred at room temperature overnight. Compound I was formed in 93% yield as determined by HPLC. The solvent was removed under reduced pressure and the oily residue dissolved in ethyl acetate and washed with acid, base, and water. The ethyl acetate phase was dried over sodium sulfate and evaporated to dryness. The residue was triturated with diethyl ether to obtain 16.6 g of compound I in 93% yield, $R_f^1$: 0.52, $R_t^A$: 7.33 min; $^1$HNMR: δ (DMSO-d$_6$, ppm), 1.39 (9H, s, BOC(CH$_3$)$_3$), 1.4–1.8 (12H, brs, β, γ, δ CH$_2$), 2.99 (4H, brs, ε CH$_2$), 3.95 (1H, m, αCH), 4.14 (1H, m, αCH), 5.03 (4H, s, Ar-CH$_2$), 6.89 (1H, d, α-urethane NH, J=7.5 Hz), 7.25 (2H, t, ε-urethane NH), 7.41 (10H, m, Ar(H)), 7.95 (1H, d, amide NH, J=8.5 Hz).

Step (II)

H(ε-Z-Lys)$_2$OH

Compound I (15.6 g, 27 mmol) was dissolved in 50 ml DCM, and cooled to 0° C. TFA (50 ml) was added to the reaction mixture and it was stirred at 0° C. for 10 min and room temperature for a further 50 min. The solvent and the excess TFA were evaporated to dryness and the oily residue triturated with diethyl ether. 15.3 g of the compound II was obtained; $R_f^2$: 0.19, $R_t^A$: 6.07 min.

Step (III)

α-BOC(ε-Z-Lys)$_3$OH

α-BOC(ε-Z-Lys)OH (8.96 g, 27 mmol) was activated by HOSU and DCCD as in example I. DCU was filtered off and the filtrate added to 15.1 g of compound II. DIEA (6 g, 46 mmol) was added to the reaction mixture and it was stirred overnight at room temperature. The solvent was evaporated and the residue dissolved in ethyl acetate and washed with acid, base and water. The ethyl acetate was dried over sodium sulfate and evaporated to dryness. The residue was triturated with diethyl ether to obtain 20 g of white precipitate of compound III in 87% yield; $R_f^1$: 0.36, $R_t^A$: 7.92 min; $^1$HNMR: δ (DMSO-d$_6$, ppm), 1.39 (9H, s, BOC(CH$_3$)$_3$), 1.4–1.8 (18H, brs, β, γ, δ CH$_2$), 2.99 (6H, brs, εCH$_2$), 3.95 (1H, m, αCH), 4.14 (1H, m, αCH), 4.34 (1H, m, αCH), 5.03 (6H, s, Ar—CH$_2$), 6.8 (1H, d, ε-urethane NH, J=7.5 Hz), 7.25 (3H, t, ε-urethane NH), 7.41 (15H, m, Ar(H)), 7.80 (1H, d, amide NH, J=8 Hz), 8.15 (1H, d, amide NH, J=8 Hz).

Step (IV)

α-BOC(ε-Z-Lys)$_3$-Ala-Tris

α-BOC(ε-Z-Lys)$_3$OH (1 g, 1.2 mmol) was dissolved in 40 ml DMF, and DSC (0.92 g, 3.6 mmol) added. After adding DIEA (0.2 ml, 1.2 mmol) and stirring at room temperature for 1 h the activated ester of the tri-Lys formed with a 78% yield as determined by HPLC. Ala-Tris (0.46 g, 2.4 mmol) was added to the reaction mixture and the pH adjusted to 8 by adding 0.6 ml of DIEA. The formation of the title compound was followed by HPLC. After 2 h the activated ester was almost fully utilised being either coupled to Ala-Tris to form compound IV or hydrolysed to the tri-Lys compound. The total yield of compound IV was 52% by HPLC. Preparative HPLC yielded 270 mg of pure compound with $R_t^A$: 7.4 min; $^1$HNMR: δ (DMSO-d$_6$, ppm), 1.39 (9H, s, BOC(CH$_3$)$_3$), 1.4–1.9 (18H, brs, β, γ, δ CH$_2$), 2.97 (6H, brs, εCH$_2$), 3.53 (6H, d, Tris (CH$_2$), J=3 Hz, 3.75–4.43 (4H, brs, αCH), 3.89 (3H, t, OH), 5.08 (6H, s, Ar—CH$_2$), 6.8 (1H, d, α-urethane NH, J=7.4 Hz), 7.19 (3H, t, ε-urethane NH), 7.41 (15H, m, Ar(H)), 7.80 (1H, d, amide NH, J=8 Hz), 8.15 (1H, d, amide NH, J=8 Hz), 8.35 (1H, d, amide NH, J=8 Hz).

Step (V)

α-BOC(ε-Z-Lys)$_3$-Ala-Tris(palmitate)$_n$, n=1,2,3

α-BOC(ε-Z-Lys)$_3$-Ala-Tris (173 mg, 0.173 mmol) was dissolved in 3 ml DCM and 1 ml DMF. Palmitic acid (89 mg, 0.346 mmol) and a catalytic amount of DMAP was added to the reaction mixture. It was cooled to 0° C. and DCCD (71 mg, 0.346 mmol) dissolved in 2 ml DCM was dropped into the reaction mixture. It was stirred at 0° C. for 30 min followed by room temperature overnight. The ratio of the title compound with mono, di, and tri palmitate compounds was 17%, 40% and 43% by HPLC (System B).

The solvent was evaporated to dryness and the residue was redissolved in DCM. The DCU was filtered off and the filtrate washed with sodium bicarbonate (5%) and water. Preparative HPLC of this mixture yielded high purity compounds of monopalmitate (17 mg, $R_t^B$: 7.63 min), dipalmitate (76 mg, $R_t^B$: 8.65 min), and tripalmitate (63 mg, $R_t^B$: 9.29 min). $^1$HNMR of the tripalmitate compound: δ (CDCl$_3$, ppm): 0.8–0.95 (9H, t, CH$_3$), 1.3–1.47 (84H, m, BOC (CH$_3$)$_3$, Palmitate (CH$_2$), Ala (CH$_3$)), 1.47–1.9 (18H, brs, β, γ, δ CH$_2$), 1.83 (6H, t CH$_2$), 2.28 (6H, t, CH$_2$), 3.09 (6H, brs, εCH$_2$), 3.97 2H, m, αCH), 4.29 (1H, m, αCH), 4.35 (6H, s, Tris(CH$_2$)), 4.47 (1H, t, αCH), 5.04 (6H, s, Ar—CH$_2$), 5.56 (1H, d, amide NH, J=7 Hz), 5.7 (1H, d, amide NH, J=7.5 Hz), 5.78 (1H, d, amide NH, J=7.5 Hz), 6.92 (1H, d, α-urethane NH, J=7.4 Hz), 7.19 (3H, t, ε-urethane NH), 7.35 (15H, m, Ar(H)).

Step (VI)

(Lys)$_3$-Ala-Tris(palmitate)$_3$

Compound V (45 mg) was dissolved in DCM (2ml) and cooled to 0° C. TFA (2 ml) was added to remove the Boc group at 0° C. for 10 min and room temperature for 30 min. The solvent and the excess TFA were removed thoroughly by repeated co-evaporation with diethyl ether. $^1$HNMR of this compound showed the disappearance of the BOC (CH3) group. The residue was then dissolved in a solution of DCM/Methanol (50/50, 4 ml) and hydrogenated for 2 h at 40 psi in a Parr Hydrogenator using 10% paladium/carbon to remove the Z groups. The removal of the Z groups was confirmed by $^1$HNMR spectroscopy (by the disappearance of chemical shifts at 5.04 and 7.35 ppm).

Biology

Abbreviations used

A=Alanine
DDME=(Depleted) Dulbeccos Modified Eagles Medium made at 2×concentration, frozen, thawed at 37° C., filtered and diluted to 1× before use (Loeffler, J-P and Behr, J-P, Methods in Enzymology (1993) H, p 599–654.
DME=Dulbeccos Modified Eagles Medium
DOPE=Dioleoyl phosphatidyl ethanolamine
EM=Electron Microscope(y)
F=Phenylalanine
FCS=Foetal Calf Serum
FLAEP=fluorescein alanine ethanolamine palmitate
FLATP3=fluorescein alanine Tris tripalmitate
G=Glycine
K=Lysine
K3ATP1-3=trilysine alanine tris mono-tri palmitate
L=Leucine
Lfe=Lipofectamine (Gibco BRL)
MTS=3-(4,5-dimethylthiazol-2-yl)-5-(3-carboxymethoxyphenyl)-2-(4-sulfophenyl)-2H-tetrazolium, inner salt; (Owen's reagent)
MTT=3-[4,5, Dimethylthiazol-2-yl]2, 5-diphenyltetrazolium bromide; Thiazole blue
PBS=Phosphate Buffered Saline
TEM=Transmission Electron Microscope
VF=Verafectin=K3ATP3
VFA3=K3ATP3
VFG2=K3GTP2

A. Cellular Uptake and Distribution

In order to assess the ability to deliver compounds into cells, preliminary experiments were conducted with fluorescein alanine ethanolamine palmitate (FLAEP) and fluorescein alanine tris tripalmitate (FLATP3).

The FLAEP and FLATP3 conjugates were diluted from DMSO solution into aqueous medium (PBS) to 10 μM and put on to a washed monolayer of subconfluent Cos 1 cells growing on boiled glass cover slips. After the incubation period as specified in the experiment, up to 24 hours exposure, the cells were washed and fixed in formaldehyde for 20 minutes. Cells were then observed under laser excitation in a Bio Rad MRC 500 confocal microscope.

Cells fixed only fifteen minutes after treatment with either FLAEP or FLATP3 exhibited intense cytoplasmic staining. Cells exposed to an equivalent level of fluorescein alone exhibited only a very weak generalised fluorescence over the whole cell. It was particularly noticeable that FLATP3 appeared to associate preferentially with the cellular and nuclear membranes, a pattern that persisted in cells allowed to grow for 24 hours despite the conjugate solution being washed off the monolayer and replaced with serum containing medium after 2 hours. This same persistence of staining was not observed with the FLAEP conjugate under the same conditions.

Fixation in 4% paraformaldehyde preserved the cellular morphology better than the formaldehyde fixative. Consequently, a higher resolution image of the fluorescence in the cell was obtained. This indicated that both conjugates appeared to localise in very discrete regions of the cytoplasm rather than displaying a generalised distribution. Observations at the light microscope level indicated that the regions of localisation may be the endoplasmic reticulum, golgi apparatus and possibly mitochondrial membranes.

Observations at lower resolution (40×objective) on live, unfixed cells done over the same periods of exposure as for fixed cells, indicated a different pattern of staining. The FLAEP conjugate appeared to enter the cell readily, but was concentrated particularly in the nucleus. This possibly indicates that this generalised cytoplasmic and nuclear distribution results from molecules which remain unattached to components of these compartments. On fixation such molecules would be washed from the cells leaving only conjugate that is bound to cellular components. FLATP3 conjugate however, exhibited a similar pattern whether the cells were live or fixed.

No overt cytotoxicity occurred in cells treated with either compound at a concentration of 10 $\mu$M for up to 2 hours. After 72 hours continuous exposure of Cos 1 cells to 50 $\mu$M or greater FLAEP. significant cytotoxicity was observed as assayed by standard MTT cytotoxicity assay (see below). After the same prolonged exposure period of 72 hours, FLATP3 caused approximately 80% cylotoxicity at 12.5 $\mu$M (relative to the same concentration of DMSO diluent) and 70% cytotoxicity at 6.25 $\mu$M.

These results clearly indicated that the lead compounds carrying fatty acyl derivatives could facilitate their own entry into cells. Observed cytotoxicity was negligible over the period required for the compound to enter the cell, but increased significantly with prolonged exposure. Accordingly, experiments were conducted to determine whether similar compounds could be used to introduce other compounds such as DNA into cells by association.

B. Transfection Experiments a) Cytotoxicity

Cytotoxicity was assayed using a standard MTT (3-[4,5x, Dimethylthiazol-2-yl]2, 5-diphenyltetrazolium bromide; Thiazole blue) assay. Briefly Cos 1 cells were seeded at $2\times10^4$ cells/well in a 96 well microtitre tray and allowed to adhere overnight in 100 $\mu$l of culture medium. Test compound was then added at 2×concentration in 100 $\mu$l of culture medium in doubling dilutions down the plate. Cells were incubated under normal culture conditions of 37° C. and 5% $CO_2$ for 72 hours. 20 $\mu$l of MTT (5mg/ml in PBS) was added for 2.5 hours at 37° C. and then all liquid removed. 100 $\mu$l of acidic propanol was added and the plate shaken for 10 minutes before reading the OD at 570 nm with ref OD 630 nm.

Figure 1A:
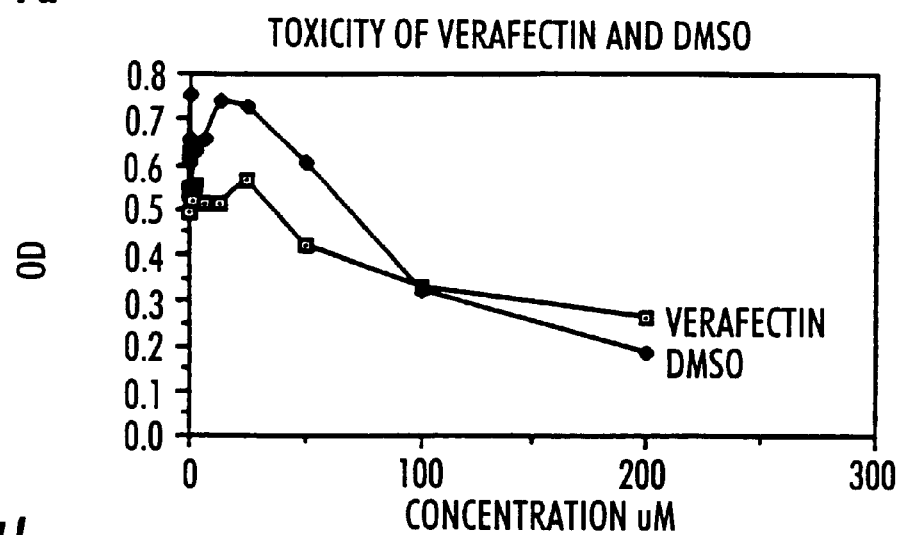
FIG. 1a shows toxicity of Verafectin and DMSO and 1b shows % survival in Verafectin compared to DMSO.
Figure 1B:
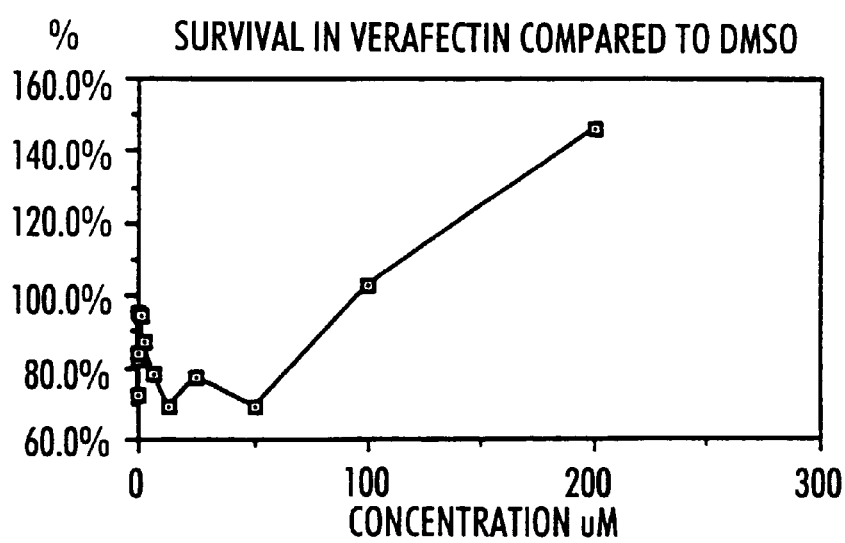

A lead compound, K3ATP3 (tri lysine alanine tris tripalmitate) called VerafectinA3, was designed which would be expected to attract DNA by virtue of its overall positive charge. It is insoluble in aqueous solution, partially soluble in warm ethanol and soluble in DMSO. Cytotoxicity was tested by exposing Cos 1 cells continuously for 72 hours to the K3ATP3 diluted from a stock of 2.5 mg/ml in 25% DMSO. There was 70% survival of cells compared to the same concentration of DMSO diluent at 12.5–50 $\mu$M compound (FIG. 1a and b). When the compound was dissolved in a similar concentration of ethanol, survival of the cells was slightly greater (FIG. 2a and b).

b) DNA Delivery

Experiment 1

To test the transfection properties of the lead compound K3ATP3 (VerafectinA3), whole uncut plasmid carrying the gene encoding CAT (chloramphenicol acetyl transferase) under the control of the SV40 late promoter, pSVLCAT (Cameron, F. H. and Jennings, P. A. (1989) PNAS 86, 9139–9143) was mixed with the test agent and put on Cos 1 cells under various conditions. After 48 hours of culture the level of secreted CAT was assayed from the culture medium.

Method

Solution I: 1 $\mu$g Plasmid DNA in 500 $\mu$l Dulbeccos Modified Eagles Medium (DME)

Solution II: 0–20 $\mu$l VerafectinA3 (2.5 mg/ml 25% DMSO) in 500 $\mu$l DME, Vortex Combine solution I and II, vortex briefly and incubate at room temperature for 10 min.

Add mix to washed cells in 60 mm tissue culture dishes (seeded $0.5\times10^6$/dish previous day) for 6 hrs at 37° C., 5% $CO_2$. Add 2 ml DME+10% FCS for remainder of 48 hrs. Assay CAT levels in tissue culture medium (Sleigh, M. J. (1986) Anal. Biochem. 156.251–256).

Result

Significant CAT levels were detected from those samples transfected with 5 $\mu$l (12.5 $\mu$g) of VerafectinA3 (2.5 mg/ml= 1.8 mM) and above. Peak CAT level was observed with 10 $\mu$l (25 $\mu$g) VerafectinA3 (FIG. 3).

Experiment 2

To compare transfection levels in Cos 1 cells using a VerafectinA3 stock solution (10 mg/ml) dissolved in either 100% DMSO or ethanol and to optimise the time of exposure of the cells to VerafectinA3 /DNA complex.

Method a—Compare VerafectinA3 dissolved in DMSO or ethanol.

b—Compare VerafectinA3 on cells 6 hrs to overnight. VerafectinA3 at 10 mg/ml in 100% solvent was diluted to 2.5 mg/ml with water.

Transfection was carried out as for experiment 1. VerafectinA3 was left in contact with the cells for varying times.

Results i) Significant levels of CAT were detected from all samples treated with 10 $\mu$l (25 $\mu$g) of VerafectinA3 and above.

(ii) Ethanolic samples exhibited reduced transfection qualities.

(iii) Overnight incubation with VerafectinA3 reduced CAT levels by approximately 50% compared to a 6 hour incubation.

Experiment 3

To compare levels of transfection achieved in CHO cells using VerafectinA3 and G2 to that achieved with commercially available reagents Transfectam (Promega) and Lipofectamine (BRL).

Method

Protocol was the same for Verafectin and Transfectam (see above) with the exception that 0.5 $\mu$g of pSVLCAT DNA was used /60 mm dish.

Lipofectamine protocol was according to manufacturer's instructions. 0.5 $\mu$g pSVLCAT/60 mm dish. CHO cells seeded $1\times10^5$/60 mm dish and adhered overnight in DME/ Hams medium with 10% FCS.

Transfectam 5 or 10 $\mu$l 1mg/400 $\mu$l stock solution.

Lipofectamine 5 or 10 $\mu$l 2 mg/ml (mixed formulation 3:1 with DOPE). VerafectinA3 (K3ATP3) and VerafectinG2 (K3G[Glycine]TP2) each at 5, 10 and 15 $\mu$l of 2 mM (2.8 and 2.3 mg/ml respectively) stock.

The serum free incubation period in the presence of test agents and DNA was 6 hours, then 1 ml DME/Hams+10% FCS was added. At 24 hrs the medium was changed to 2 ml of fresh DME/Hams+10% FCS until harvest at 48 hrs.

Results
CHO cells were lysed 48 hrs after starting the transfection step and assayed for CAT activity. Peak transfection was observed with 5 μl of transfection agent in all cases. CAT levels obtained using VerafectinA3 were approximately 54% of those obtained with Transfectam and 18% of those obtained with Lipofectamine.

CAT levels obtained using VerafectinG2 were approximately 64% of those obtained with Transfectam and 22% of those obtained with Lipofectamine. See FIG. 4.

Experiment 4

To compare levels of transfection achieved in Cos 1 cells using VerafectinA3 (K3ATP3) and VerafectinG2 (K3GTP2) to that achieved with the commercially available reagent Lipofectamine (BRL).

Protocol was the same for the Verafectins as described above. Lipofectamine protocol was according to manufacturers instructions. Cos 1 cells were seeded at $5 \times 10^5$/60 mm dish and adhered overnight in DME with 10% FCS.

Solution A: 0.5 μg pSVLCAT/60 mm dish.
Solution B: Lipofectamine 10 and 15 μl 2 mg/ml (mixed formulation 3:1 with DOPE).
OR; VerafectinA3 and VerafectinG2 20 μl 2 mM (2.8 and 2.3 mg/ml respectively) stock.
OR; VerafectinG2 was also tested with an equimolar amount of DOPE. VerafectinG2 and DOPE were mixed in DDME and vortexed for 30 seconds before use.
Solutions A and B were combined before overlaying on washed cells.

The serum free incubation period in the presence of test agents and DNA was 6 hrs, then 1 ml DME+10% FCS was added. At 24 hours medium was changed to 2 ml fresh DME+10% FCS until harvest at 48 hrs.

Results

Tissue culture media samples from Cos 1 cells (supernatants) were assayed for CAT activity 48 hours after starting the transfection step. VerafectinA3 and VerafectinG2 transfected Cos 1 cells to levels approximately 60% and 30% respectively, of that achieved using Lipofectamine. The addition of equimolar unformulated DOPE (2 mM in DMSO/H$_2$O) to a VerafectinG2 sample resulted in an approximate doubling of transfection efficiency compared to VerafectinG2 alone, bringing it to the order of 60% of that achieved with Lipofectamine and equal to VerafectinA3. CAT levels obtained are shown in FIG. 5.

C. Relative Cytotoxicity

Relative levels of cytotoxicity caused by the different agents were compared during the experiment using the dye "Alamar Blue" (Alamar, Sacramento Calif.). Compounds of the invention type generally exhibited significantly lower cytotoxicity than the other agents.

Figure 6A:
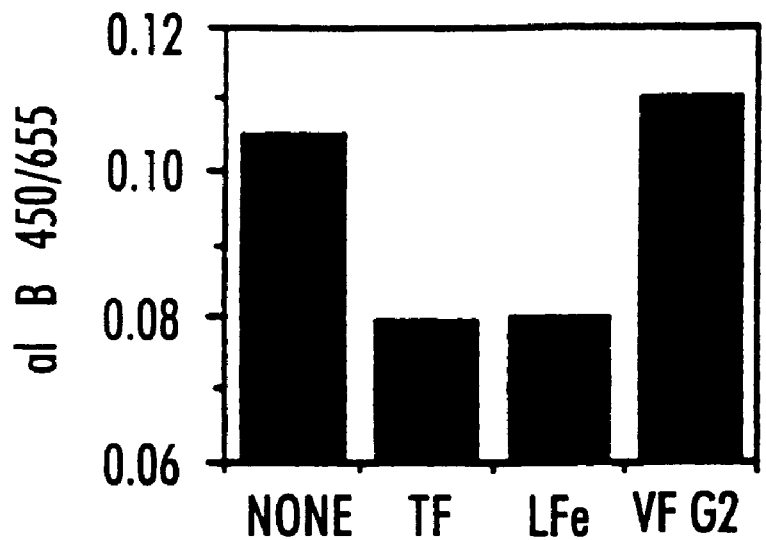

For example FIGS. 6a and b

Relative levels of cytotoxicity were also assayed in subsequent experiments using the dye MTS, marketed as Cell titre 96 Aqueous (Promega).

D. Relative Efficiencies of Variants of the Lead "Transfection" Compounds

Cell lines Cos 1 or CHO were transfected with 0.5 μg of pSVLCAT or 2 μg of pPGKlacZ plasmid using a range of concentrations of each transfection compound. The optimal concentration of compound, that is the concentration giving the highest level of CAT at 48 hours or the greatest percentage of lac z (β-galactosidase) staining cells at 24 hours was used to collate data for Table 1. As all compounds were not tested in a single experiment, absolute figures indicating transfection were not used. Rather, symbols are used to indicate the transfection efficiency relative to Lipofectamine (BRL), which was included as a control in all experiments. Table 1 thus indicates the relative efficiencies of a number of compounds in mediating the transfection of at least one cell type.

TABLE 1

Relative Efficiencies of Transfection Achieved by Test Compounds as Assessed by Reporter Gene Expression

| Compound | Cell Type | Transfection (CAT) | Transfection (βGal) |
|---|---|---|---|
| Lipofectamine | Cos 1 | +++++ | 8–10% of cells |
|  | CHO | +++++ | 8–10% of cells |
| Transfectam | Cos 1 | ++++ | nd |
|  | CHO | ++++ | nd |
| Lipofectin | Cos 1 | +++(+) | nd |
| K3 | Cos 1 | − | nd |
| K3ATP0 | Cos 1 | − | nd |
| K3ATP1 | Cos 1 | + | nd |
|  | CHO | + | nd |
| K3ATP2 | Cos 1 | +/− | nd |
|  | CHO | +/− | nd |
| K3ATP3 | Cos 1 | +++(+) | nd |
|  | CHO | +++ | nd |
| K3GTP0 | Cos 1 | − | nd |
| K3GTP1 | Cos 1 | + | nd |
|  | CHO | + | nd |
| K3GTP2 | Cos 1 | ++ | nd |
|  | CHO | +++ | <1% |
| K3GTP3 | Cos 1 | +/− | nd |
|  | CHO | + | nd |
| K4ATP2 | Cos 1 | + | nd |
| K4ATP3 | Cos 1 | +(+) | <1% |

Experiments were carried out as described in Experiment 1 of Section B above with variations described in Experiment 3. Results shown were derived from optimised levels of transfection agent. All results shown were generated by the authors; company literature accompanying commercial agents was not included. Other variant compounds synthesized and tested are described below.

Conclusion

Results shown in the above table indicate that all compounds tested which had K1–4, A or G linker and Palmitate 1–3 were capable of some level of transfection in the cell types tested. Compounds which were missing either a lysine or a palmitate were not able to support transfection indicating the requirement for both the DNA attracting moiety (K) and the presumptive cell penetrating moiety (palmitate). The different linkers had an effect on the level of transfection but were both capable of supporting transfection.

Variations on the lead compound alter transfection efficiency

The compounds of the generic formula described on page 3 were addressed as consisting of the described basic building blocks: "x, y, R1–R4". These components were systematically varied to assess the optimal building blocks for transfection of standard cell lines in a standard assay system. Results will be presented by the use of example experiments, and shown as the levels of reporter gene expression achieved under standard conditions by either overall levels (CAT or β-galactosidase expression) or as % cells transfected (β-galactosidase—blue cells). Representative levels of cytotoxicity will also be described.

"x" Peptide

The lead compound "VerafectinA3" described above carried 3 lysine residues (K3) imparting a charge of 4$^+$ to the molecules. Variants were tested which carried K0 to K5 carrying 0$^+$ to 6$^+$ respectively.

Aim

To assess the optimal number of K residues for efficient transfection.

Method

In separate experiments, comparisons were carried out between:

a. K0ATP3, K3ATP3, K5ATP3 and K2ATP2, K5ATP2 (CHO cells)

b. K1ATP2, K2ATP2 (Cos 1 cells).

c. K3ATP3, K4ATP3, K5ATP3 (CHO cells)

All test lipopeptide reagents were originally dissolved at 10 mM in 75% DMSO, and subsequently diluted with water to make a 2 mM stock stored at 4° C. Volumes of 2 mM stock lipopeptide ranging from 2 $\mu$l to 15 $\mu$l were diluted in 500 $\mu$l of DDME. 1 $\mu$g of plasmid pSVLCAT was separately diluted in 500 $\mu$l of DDME. Solutions were combined for 10–20 min at room temperature before adding to 500 $\mu$l of DDME in 60 mm dishes of subconfluent CHO cells ($2\times10^5$ day–1) or Cos 1 cells ($5\times10^5$ day–1); washed free of serum with DDME.

Cells were incubated for 6 hrs under standard conditions of 37° C. and 5% $CO_2$ for 6 hours. 1.5 ml of DME/Hams+ 10% FCS (CHO) or DME+10% FCS (Cos 1) was added to the cells for overnight incubation. Fresh DME/Hams+10% FCS or DME+10% FCS was used to replace the medium for a further 24 hours prior to harvest. Cell lysates were prepared and assayed for CAT activity as described above. For Cos 1 cells, culture supernatants were assayed for CAT activity.

Results a: In the tripalmitate compounds K3ATP3 resulted in good transfection (mean of 6237 cpm from 25 $\mu$l lysate after 20 min assay time at 37° C., 1 $\mu$l $C^{14}$ acetyl CoA (total available counts ˜40–50,000 cpm)). The K5 compound gave significantly reduced counts at its optimal level (mean 1785 cpm). The K0 compound gave no measurable transfection in this assay system, however, low levels of transfection were observed using the $\beta$-gal assay system (described below) in CHO cells.

With the dipalmitate compounds, the presence of K2 was significantly superior for transfection giving a mean of 5418 cpm, compared to a mean of 132 cpm for the K5 compound. Viability of the transfected dishes of cells is indicated in graph 7b. Toxicity is highest (OD lowest) in the dishes exhibiting highest levels of transfection.

See FIGS. 7a and b b: The inclusion of a single K did enable significant transfection to occur, with a mean of 12670 cpm (25 $\mu$l lysate, 135 min incubation 37° C., 2 $\mu$l $C^{14}$ acetyl CoA (total available counts ˜90–100,000 cpm)). The presence of a second lysine residue resulted in nearly 5 times the transfection levels (mean 62,215 cpm), with the optimal results occurring at the same level of compound.

FIG. 8 c: Both K4ATP3 and K5ATP3 compounds resulted in significantly reduced transfection in relation to the K3 equivalent giving a mean level of CAT activity measured at 1071, 6363 and 13467 cpm respectively after 2 hours incubation of 20$\mu$l of lysate.

FIG. 9

Conclusion

From the data shown, an ordering of optimal activity between the inclusion of 0 to 5 lysines on $K_{n=1 to 5}$ ATP2/3 can be drawn as follows:

$K3 \geq K2 > K5 > K4 >> K1.$

A representative graph of cell viability is shown for experiment b, (see FIG. 7b). This indicates an inverse relationship between cell viability and transfection. This is a common finding.

"y" Linker

The lead compound described above carried 3 lysine residues (K3) and an Alanine (A) linker at the "y" position. Variants were tested which carried Alanine (A), Leucine (L), Phenylalanine (F), Lysine (K) or Glycine (G).

Aim

To assess the optimal linker residue for efficient transfection.

Method

In separate experiments, comparisons were carried out between:

| a. | K2 | K/F/L | TP2 | (Cos 1) |
| b. | K2 | A/L | TP2 | (Cos 1) |
| c. | K3 | A/L/G | TL3 | (Cos 1) |

For transfection of pSVLCAT and subsequent assay of CAT enzyme, experiments "a" and "b" were carried out as described above.

For experiment "c", a plasmid pPGKlaczNLS encoding $\beta$-galactosidase under the control of the mouse PGK promoter (kind gift from G.Hannan) or pSVGAL which utilises the SV40 early promoter (Sleigh, M. J. and Lockett, T. J. (1985). EMBO J. 4:3831–3837),was transfected. This experiment and assay were modified from Feigner et al J. Biol Chem. 269(4) 2550–2561 1994. This protocol allows the simultaneous assessment of 72 different combinations and concentrations of DNA and test agent in a microtitre tray. The well exhibiting the maximal level of gene product was chosen as the optimal result for each reagent. Cytotoxicity was assessed using alamar blue, and a sample graph is shown for experiment a.

Results a: In a comparison of linkers K, F and L in a dilysine, dipalmitate compound, L gave marginally superior results to F, but was substantially more effective than the K compound. See FIG. 10a. Toxicity of the L and F compounds was somewhat higher than for the K compound indicating that the higher CAT levels were not seen simply because of higher cell survival levels.

FIG. 10b.

b: In a comparison between the A linker used in the peptide comparison experiments and the L linker shown to give higher levels of gene expression in experiment "a", the two compounds were shown to have very similar activities.

FIG. 11.

c: The two leading linkers A and L were tested in a background of trilysine, trilaurate (L3) against a G linker. In this case, the A linker compound was superior in achieving transfection, with the other compounds showing relative transfection levels of: L 57%, G 12% and Lipofectamine 39%.

FIG. 12.

Conclusion

From a comparison of the data presented, an order of effectiveness of different linkers can be drafted:

$A \geq L > F > K >> G.$

"R1–R4" Fatty acyl derivatives

I. Number of acyl derivatives on tris linker, 1 to 3

The tris linker provides the facility to add one, two or three fatty acyl derivatives to the peptide and linker. Generally all of these derivatives would be identical to each other. Compounds bearing all identical building blocks but carrying one, two or three fatty acyl derivatives, have been compared using the standard transfection and assay procedures described above.

Aim

To compare the ability of peptide fatty acyl derivative compounds carrying one, two or three fatty acyl derivatives, to transfect mammalian cells.

Method

Compounds were tested for their ability to transfect either the CAT or β-gal gene carried on plasmids, and assayed as described above.

Experiments

| a. | K2 A T | P1/P2/P3 (Palmitate, 1, 2 or 3) | (Cos 1) |
|---|---|---|---|
| b. | K2 F T | P1/P2/P3 | (Cos 1) |
| c. | K2 L T | P1/P2/P3 | (Cos 1) |
| d. | K2 K T | P2/P3 | (Cos 1) |
| e. | K3 A T | P2/P3 | (CHO) |
| f. | K3 A T | P1/P3 | (Cos 1) |
|  | K3 A T | M1/M2/M3 (Myristate 1, 2 or 3) | (Cos 1) |
|  | K3 A T | L1/L2/L3 (Laurate 1, 2 or 3) | (Cos 1) |
| g. | K4 A T | P1/P2/P3 | (Cos 1) |

Results a: A comparison of the compounds tested in experiment "a" showed that the di and tri palmitate molecules both give high levels of transfection whereas the monopalmitate molecule is very inefficient.

FIG. 13a.

In other experiments the K3 monopalmitate compound has shown activity at 30% of the tripalmitate K3 molecules (not shown). Relative cytotoxicity of the compounds is shown in the accompanying graph,

FIG. 13b.

b: Relative transfection abilities of mono, di and tripalmitate compounds with a phenylalanine linker were similar to those with an alanine linker (a).

FIGS. 14a and b.

c: Relative transfection abilities of mono, di and tripalmitate compounds with a leucine linker were similar to those with an alanine linker (a).

FIGS. 15a and b.

d: In the case of the lysine linker, the dipalmitate is shown to be significantly less active than the tripalmitate molecule. The increased transfection activity of the tripalmitate is concomitant with an increase in cytotoxicity as seen in previous cases.

FIGS. 16a and b.

e: In this comparison, the tripalmitate molecule is dramatically more efficient (mean of 8325 cpm) than the dipalmitate (mean of 984 cpm). Levels of cytotoxicity are somewhat greater with increased transfection.

FIGS. 17a and b.

f: In this comparison, where compounds with different numbers of fatty acyl groups (n=1 to 3) are compared for transfection efficiency in backgrounds of 3 different length fatty acyl derivatives (palmitate, myristate and laurate) the compounds with 3 fatty acyl groups were shown consistently to be more effective in transfection than those with 2 groups or 1 group. Toxicity in the presence of 3 fatty acyl groups was generally slightly higher but always less than with lipofectamine. See table 2.

TABLE 2

| Test agent | ratio [lipid]/[DNA] | units β-gal | MTS OD$_{490-655}$ |
|---|---|---|---|
| K3ATP1 | (5.55) | $9.32 \times 10^{-6}$ | 1.34 |
| K3ATP3 | (0.69) | $2.73 \times 10^{-4}$ | 1.244 |
| K3ATM1* | (0.69) | $5.85 \times 10^{-6}$ | nd |
| K3ATM2 | (0.35) | $3.46 \times 10^{-5}$ | 1.56 |
| K3ATM3 | (1.39) | $2.86 \times 10^{-4}$ | 1.22 |
| K3ATL1* | (0.35) | $1.09 \times 10^{-5}$ | nd |
| K3ATL2 | (0.69) | $1.06 \times 10^{-5}$ | 1.554 |
| K3ATL3 | (1.39) | $4.95 \times 10^{-4}$ | 1.363 |
| Lfe | (1.39) | $4.65 \times 10^{-4}$ | 0.924 |
| NONE |  | $-5.62 \times 10^{-6}$ | 1.482 |

Each result displayed is the highest reading from a microtitre plate of 72 different conditions. The ratio of [lipid]/[DNA] at which that maximum was achieved is shown. Experiments shown were carried out in Cos 1 cells, as described above. MTS OD is a measure of relative viability of the cells exposed to the different agents, a higher value indicates greater cell viability. * These points were taken from a separate experiment and some slight variation between absolute numbers should be expected between experiments. Viability was measured with the dye alamar blue in this experiment and is thus not directly comparable.

g. K4 compounds

A comparison was made between one to three palmitates in a background of tetra lysine alanine (K4ATP1/2/3). As seen in the previous experiments, the tripalmitate was more effective than the di or monopalmitate. Activity was measurable when using any one of the compounds. Cytotoxicity was low these reagh high levels of these reagents were required for optimal transfection.

FIGS. 18a and b.

Conclusion

Results from experiments with "K3" compounds, are similarly seen with "K4" compounds. That is, three fatty acyl groups are superior to two or one group in their ability to transfect cells.

Conclusion section R1–R4

As shown in the above examples, compounds with three fatty acyl derivatives generally show a greater ability to transfect the cells than those with one or two fatty acyl derivatives. At the optimal points of transfection, the compounds are generally significantly less toxic to the cells than the commercial agent "Lipofectamine". Although most of the data presented in this segment is from experiments carried out on Cos 1 cells, these results were reflected in the results obtained on CHO cells. Optimal concentrations for different compounds varied between cell lines, as did absolute levels of gene product, however the optimal ratio between [lipid]/[DNA] was generally cell independent, and the relative positions of the compounds in transfectability remained similar. A comparison of the data presented allows an order of effectiveness of different numbers of fatty acyl groups (n=1 to 3) of unformulated unmixed compounds to be drafted:

3>2>1.

"R1–R4" Fatty acyl derivatives
II. Length of Carbon Chain

Aim

To determine whether fatty acyl derivatives of different length to C16 (Palmitate) had greater ability to transfect mammalian cells.

Method

Variant compounds of trilysine alanine tris (K3AT) were generated bearing one to three identical fatty acyl derivatives varying in length as follows:

C16 Palmitate (P)

C14 Myristate (M)

C12 Laurate (L)

C10 Caproate (C)

Each of these compounds was tested for transfection ability and cytotoxicity on standard cell lines using standard conditions as described above.

Results a. Comparisons between P, M, L and C derivatives in Cos 1 and CHO cells. This table shows that compounds with Laurate and Myristate are generally able to transfect cells more efficiently than the palmitate derivatives originally used. Caproate was the least active derivative in these compounds.

TABLE 3

| Agent | β-gal (Cos 1) | Viability (Cos 1) | β-gal (CHO) | Viability (CHO) |
|---|---|---|---|---|
| K3ATL1(.35)(2.77) | $1.09 \times 10^{-5}$ | 0.104 | $2.99 \times 10^{-6}$ | 0.072 |
| K3ATM1(.69)(.69) | $5.85 \times 10^{-6}$ | 0.102 | $5.18 \times 10^{-6}$ | 0.07 |
| K3ATP1(5.55) | $9.32 \times 10^{-6}$ | 1.34* | | |
| K3ATL2(.69) | $1.06 \times 10^{-5}$ | 1.55* | | |
| K3ATM2(.35) | $3.46 \times 10^{-5}$ | 1.56* | | |
| K3ATC3(2.77) | $9.08 \times 10^{-6}$ | 0.104 | $5.27 \times 10^{-6}$ | 0.052 |
| K3ATL3(.69)(.69) | $3.02 \times 10^{-4}$ | 0.095 | $7.89 \times 10^{-4}$ | 0.027 |
| K3ATP3(1.39) | $3.52 \times 10^{-5}$ | 0.077 | | |
| #K3ATL3(1.39) | $4.95 \times 10^{-4}$ | 1.36* | | |
| #K3ATM3(1.39) | $2.86 \times 10^{-4}$ | 1.22* | | |
| #K3ATP3(.69) | $2.73 \times 10^{-4}$ | 1.24* | | |
| Lfe(1.39) | $1.71 \times 10^{-4}$ | 0.082 | | |
| None | $3.10 \times 10^{-6}$ | 0.11 | $3.97 \times 10^{-6}$ | 0.059 |
| Lfe(1.39) | $4.65 \times 10^{-4}$ | 0.924* | | |

Legend

Each result displayed is the highest reading from a microtitre plate of 72 different conditions. The ratio of [lipid]/[DNA] at which that maximum was achieved is shown in brackets for the two different cell types in the following order; (Cos 1) (CHO). Experiments shown were carried out in Cos 1 cells, as described above. Viability was measured with the dye alamar blue . # Denotes compounds tested in a separate experiment. * Viability in this experiment was determined with MTS. OD is a measure of relative viability of the cells exposed to the different agents, and as with alamar blue, a higher value indicates greater cell viability.

b. R1–R4 as C10 to C16 tested on Hela cells

Aim

To determine whether the most effective fatty acyl group tested in Cos 1 and CHO cells, was also the most effective in Hela cells.

Method

Hela cells were seeded in place of Cos1 or CHO cells in DME+10% FCS at a density of $2 \times 10^4$/well and transfected with pPGKlaczNLS as described above. At 48 hours, toxicity was determined by alamar blue and the cells processed for the β-gal assay.

Results

Results of the β-gal assay indicated that, as in the Cos 1 and CHO cells, as the carbon chain length decreased from C16 to C12 the transfection ability increased . When the C10 molecule was used, transfection ability was seriously curtailed indicating a peak transfection efficiency at C12 in this series. Unexpectedly, the peak level of cell viability also occurred with the C12 compound (K3ATL3).

FIGS. 19a and b.

Conclusion

The change in length of the fatty acyl derivatives has a dramatic effect on the ability of the compounds to transfect several cell types. The order of transfection is maintained in all the cell types in which they were tested. Both myristate and laurate in this position give greater levels of transfection than the prototype palmitate, with laurate superior to all tested.

"y" linker—non standard amino acids

A range of amino acids has been used as the linker group. These include leucine, glycine, alanine, phenylalanine, α-BOC (ε-free) lysine as addressed above. In addition, non-standard amino acids such as amino butyric. amino caproic and amino caprylic acids (which provide for linker length extensions of 3, 5 and 7 carbon-carbon single bonds respectively) have also been tested.

Experiment 1

Aim

To determine the transfection properties of compounds with greater length of spacing between the Tris and charged peptide "x" by utilising non—standard amino acid linkers of varying lengths at position "y".

Method

Peptide/fatty acyl conjugates were synthesized using the non-standard amino acids amino butyric (C3), amino caproic (C5) and amino caprylic (C7) acids as the linker groups, a tri-lysine nucleic acid binding domain and laurate for the three fatty acyl groups. In these new conjugates the DNA binding and tris/fatty acyl moieties were separated by an extra 3, 5 and 7 carbon bond lengths respectively when compared with the prototype molecule. These compounds were then tested in the standard manner described above to determine their relative capacity to transfect cells.

Results

K3 "y" TL3 compounds, where y=C3, C5, C7, A, L, G were compared for transfection efficiency to each other and the commercial agent Lipofectamine using the standard β-gal reporter gene system described above. All of the compounds except K3GTL3 were found to be more efficient at transfection than Lipofectamine. C3, C5, and particularly C7 compounds were shown to be dramatically more efficient than compounds using the standard single amino acid linker.

FIG. 20a.

Cytotoxicity of the agents is shown in the accompanying graph. FIG. 20b Note that the increased levels of transfection are not concomitant with an increase in cytotoxicity.

Experiment 2

Proportion of cells transfected

Aim

To determine whether the increase in transfection exhibited by the C3–C7 compounds is reflected in an increased proportion of cells transfected.

Method

These conjugates were used to transfect CHO and Cos 1 cells with pPGKlacZNLS for estimation of the proportion of cells transfected. The transfection conditions used were as described above for the CAT experiments with cells being grown in 35 mm dishes for transfection. Cells were seeded the day prior to transfection at a density of $3.4 \times 10^5$/dish (Cos 1) or $6.8 \times 10^4$/dish (CHO). After the viability analysis at 24 hrs post-transfection, the cells were washed 2× in PBS then fixed for 5 min at 4° C. in 0.2% glutaraldehyde in 0.1M phosphate buffer, pH 7.3. Cells were washed 2× with cold PBS. Fresh staining solution (10 ml 0.1M phosphate buffer, pH 7.3; 1.0 ml of a 1:1 mix of 105 mg potassium ferrocyanide in 2.5 ml $H_2O$ and 82 mg of potassium ferricyanide in 2.5 ml $H_2O$; 0.2 ml of 2% X-gal in dimethyl formamide, 11.2 μl of 1M $MgSO_4$) (2 ml) was added to each dish and dishes were incubated at 37° C. until colour developed. Random fields of cells were examined under the light microscope and the proportion of blue (β-GAL expressing) cells was determined.

Result

Increased transfection observed with the test agents was reflected in an increased proportion of cells transfected as shown by the number of blue staining cells. FIG. 21a shows the results obtained with CHO cells while FIG. 21b shows the results with Cos 1 cells. On the X axis of these panels, Lfe indicates lipofectamine; vf, the prototype peptide/fatty acyl conjugate K3ATP3; A, K3ATL3 while C3, C5, C7 represent the amino butyric, amino caproic and amino caprylic acid linked conjugates respectively.

FIGS. 21a and b

Conclusion

Increasing the length of the linker portion of peptide/fatty acyl conjugates dramatically improves their transfection properties both in overall levels of reporter gene expression and also in the proportion of cells transfected. It is particularly noticable that peak levels of transfection are achieved using these reagents at a relatively low level of toxicity. These agents do not follow the earlier observation that increased levels of transfection are directly linked to increased levels of cytotoxicity. This improved capacity of conjugates with longer linkers to promote transfection appears to be independent of cell type. The data shown in FIGS. 22a and b indicate that the amino caprylic acid linked conjugate, K3C7TL3, is also a more effective transfection reagent than lipofectamine with the human prostate cancer epithelial cell line PC3 (FIG. 22a) and the Jurkat T cell line (FIG. 22b).

FIGS. 22a and b

Cell types tested

As described above, conjugates of the generic formula described have been used to successfully transfect several cell types. A more complete list is provided below:

| Cell line | Cell description | Cells transfected plasmids transfected |
|---|---|---|
| Cos 1 | African Green Monkey fibroblasts | pSVLCAT pGKlaczNLS pSVGAL |
| CHO | Chinese Hamster Ovary cells | pSVLCAT pGKlaczNLS pSVGAL |
| Hela | Human carcinoma cells | pGKlaczNLS |
| PC3 | Prostate cancer epithelial cells | pGKlaczNLS pSVGAL |
| Jurkat | Human T Lymphocytes | pGKlaczNLS pSVGAL |
| CSL503 | Ovine epithelial cells | pGKlaczNLS pSVGAL |

Oligonucleotide transfection Aim

To determine whether compounds which have shown the capacity to transfect reporter genes on whole plasmids to cells are also efficient in the transfection of oligonucleotides.

Method

An 18-mer 5'-fluoresceinated phosphorothioate oligonucleotide was transfected into CHO cells. A comparison was made between the ability of K3C7ATL3, K3ATL3 and no-agent, to transfect the oligonucleotide into the cells. The oligonucleotide was serially diluted from 121.2 μM nucleotide, to 60.6 and 30.3 μM nucleotide. The test lipopeptides were serially diluted from 84 μM, to 42 and 21 μM. These dilutions were combined in a 3×3 matrix resulting in concentrations half that described. That is, the top dilution of oligonucleotide became 60.6 μM nucleotide (3.37 μM 18-mer oligonucleotide) and lipopeptide 42 μM. The mix was allowed to incubate for 10 min at room temperature and then overlayed on CHO cells (seeded at $1 \times 10^4$/well the previous day). washed free of serum with DDME, in a total volume of 100 μl. Wells receiving mix with no test agent had the three different concentrations of oligonucleotide overlayed under the same conditions.

After 3 hours of incubation under standard conditions of 37° C. and 5% $CO_2$, the mix was removed and replaced with 50 μl of DDME. The cells were viewed live under the confocal microscope. The level of fluorescence was so high that the pinhole aperture for the LASER on the BioRad MRC 500 confocal microscope, was shut down to minimum. All images were then collected on the same settings for a quantitative comparison.

After confocal analysis, 100 μl of EMEM+10% FCS was added back to the wells and cells were incubated under standard conditions overnight. Cells were re-examined for fluorescence.

Results

Results of transfection at the 3 hour post-transfection time point are presented in table 4:

TABLE 4

| Test agent | % cells fluorescing [test agent]μM | | | | apparent toxicity [test agent]μM | | | |
|---|---|---|---|---|---|---|---|---|
| [nucleotide]μM | 42 | 21 | 10.5 | 0 | 42 | 21 | 10.5 | 0 |
| K3C7TL3 | | | | | | | | |
| 60.6 | 100 | 100 | 100 | | ++++ | ++ | – | |
| 30.3 | 100 | 100 | 100 | | +++ | + | – | |
| 15.15 | 100 | 100 | 100 | | ++ | +++ | ++ | |
| K3ATL3 | | | | | | | | |
| 60.6 | 100 | 100 | 100* | | ++++ | + | – | |
| 30.3 | 100 | 100 | 100* | | +++ | ++ | – | |
| 15.15 | 100 | 100 | 100 | | ++ | ++ | – | |
| No Agent | | | | | | | | |
| 60.6 | | | | 4 | | | | – |
| 30.3 | | | | 11 | | | | – |
| 15.15 | | | | 2 | | | | – |

*less strongly fluorescing
More "+" = greater cell death or toxicity; 4+ being >90% cell death "–" = no obvious toxicity Conclusion The use of either transfection agent results in 100% of surviving cells taking up high levels of oligonucleotide. At the 3 hour time point described in the experiment the cell nuclei were intensely stained with fluorescenated oligonucleotide.

Results marked with an asterisk "*" were less strongly fluorescing than those unmarked, with the exception of the no-agent experiment. With no-agent the levels of fluorescence were restricted to a single spot of varying intensity in each of the cells fluorescing, at the level of detection used for the experiment.

It is likely that a larger proportion of cells than specified in table 4 took up oligonucleotide in the absence of transfection agent, but the amount of uptake was insufficient to register at the level of detection used. After overnight incubation with full medium (EMEM+10% FCS) the levels of fluorescence were reduced in all samples, the most notable change being the loss of fluorescence in most nuclei, with a punctate cytoplasmic staining being typical. Levels of fluorescence in samples which used a transfection agent remained substantially higher than those samples which did not use a transfection agent.

Formulation

Most of the commercially available transfection compounds are formulated liposomes with the neutral lipid dioleoyl phosphatidyl ethanolamine (DOPE). Additionally, it is suggested in the literature that compounds with two fatty acyl derivatives are more likely to form stable liposome structures than those compounds with one or three fatty acyl derivatives, and indeed the commercial agents invariably have two acyl derivatives. In the light of the results above which indicate that the shorter chain fatty acyl derivatives, and particularly laurate, display an increased capacity to transfect cells, it may be that the use of shorter chain phosphatidyl ethanolamine compounds may also indicate a more efficient transfection. Thus the use of DOPE should be seen in this manner as illustrative in its capacity to form effective liposome structures for transfection, and not restrictive.

Aim

To test the efficacy of Liposome formulations with the lipid DOPE.

Method

Verafectin A2 (K3ATP2) was formulated into liposomes using standard methods (K.Yagi et al. Biochem. Biophys. Res. Comm. 196 3.,1993 pp 1042–1048) and taken up into $H_2O$ at 2 mM. Formulations were made at 1:2, 1:1, and 2:1 molar ratios with DOPE.

The liposome formulations were compared to commercial compounds as described in the separate experiments below:

a. Using the standard transfection procedure described above, and 1 µg plasmid pSVLCAT, these formulations were tested on CHO cells at a single concentration equivalent to 10 µl of Verafectin A2 (2 mM) per sample and compared to unformulated compound and Lipofectamine in the same cell type. CAT production was assayed 48 hours after transfection.

b. The liposome formulations were also tested at the same concentrations using a plasmid encoding β-gal expression, pPGKlacz and compared to Lipofectamine and DOTAP (Boehringer Mannheim). 24 hours after transfection, the cells were fixed and stained for β-gal expression.

Results a. Use of the liposome formulations resulted in CAT expression from CHO cells ranging from 62% to 156% of optimal Lipofectamine induced expression using the three different ratios in two separate experiments. Use of the VFA2 compound in non-liposome formulation gave CAT levels of only around 5% of Lipofectamine. DOPE alone, either unformulated or "formulated" through the liposome procedure, gave no transfection. NB. DOPE alone does not form a true liposome, see EM section below.

FIG. 23a.

b. Preliminary cell counts of stained vs unstained cells indicated that the best liposome formulation (K3ATP2:DOPE 1:2) gave double, and DOTAP gave approximately half the number of transfected cells relative to that achieved with Lipofectamine. The proportion of CHO cells transfected using Lipofectamine under these conditions was determined to be 17.5%.

FIG. 23b.

The concentration of agent was not optimised for these Verafectin A2/DOPE formulations. Data from Lipofectamine and DOTAP however were from optimised concentrations.

Preliminary data indicate that cytotoxicity of these formulations was roughly equivalent to Lipofectamine and DOTAP (not shown).

Electron microscopy

Solutions of formulated and unformulated compounds were analysed for potential membrane-like structure. In separate experiments the following samples were analysed:

a: Negatively stained samples of formulated compounds K3ATP2:DOPE, DOPE and the unformulated compounds K3C7ATL3 and Lipofectamine.

b: Rotary shadowed samples of K3C7ATL3 and Lipofectamine mixed with two ratios of nucleotide (plasmid).

Method

NEGATIVE STAINING

Stock samples of liposomes at 2 mM, were diluted 1 in 10 with filtered distilled water, and mixed 1:1 with filtered negative stain (Ammonium Molybdate 2%, pH 6.5) and spread onto carbon-formvar coated copper/rhodium 200 mesh electron microscope grids, and examined in a Jeol JEM 100CX electron microscope at 60 kV at magnifications of between 33 k and 100 k.

ROTARY METAL—SHADOWING

Ratios of 0.69, and 0.25, of liposome:1 mole DNA nucleotides were diluted in water and mixed for 10 min at room temperature, spread onto carbon-formvar coated grids and rotary metal-shadowed with platinum-palladium (60:40) evaporated at an angle of 7° and examined in the electron microscope at 60 kV at magnifications between 26 k and 66 k.

Results a: In order to determine the successful formation of liposomes, negatively stained samples of formulated K3ATP2:DOPE were analysed in the TEM. These samples were shown to have formed multilamellar liposome structures, whereas DOPE alone did not under the same conditions.

As a formulated liposome was capable of giving efficient transfection it was of interest to see whether the pure unformulated compounds, which gave efficient transfection, had any membrane like structure. Some of these compounds were thus negatively stained and again analysed on the TEM. Interestingly these compounds which gave efficient transfection and had 3 fatty acyl derivatives, were found to have spontaneously formed "rafts" or "stacks" of membrane-bound vesicles ranging in size from 10 nm to 0.2 µm.

b: Compounds were mixed with plasmid DNA in suboptimal (0.25) and optimal (0.69) ratios of lipopeptide : nucleotide and rotary shadowed. Analysis of these samples showed dramatically that at the optimal ratio for transfection most of the DNA was incorporated into collections of liposomes. At ratios where insufficient compound was present (0.25:1), a large amount of DNA was free in the solution. This was true both for the test compound K3C7TL3 and Lipofectamine, which appeared very similar under EM when mixed with DNA although their appearance uncomplexed with DNA was very different.

Unformulated mixtures of transfection compounds and other lipids

There was a discrepancy between the proportion of cells transfected by oligonucleotides (100% fluorescing cells) and those which expressed a gene product (<100% blue cells). As it is necessary for DNA to be taken into the nucleus, transcribed and translated to achieve a gene product, whereas oligonucleotide only has to get through the plasma membrane to achieve "transfection", this was not a surprising result. However, it does indicate that successful transfection and generation of a gene product is a multistep procedure which could benefit from a combination of compounds which may have differential capacities to cross different membranes, for example the plasma and nuclear membranes.

With this in mind a number of otherwise identical compounds bearing different fatty acyl groups differing in both number and length were combined and tested in the β-gal plate assay as detailed below.

Improvements in transfection by some compounds have also been seen by the simple addition of the neutral lipid DOPE as seen above in experiment 4 using VerafectinG2 (K3GTP2).

Aim

To determine whether mixtures of lipopeptide compounds of the generic formula described in this application, have an advantage in gaining transfection of genes as assayed by the display of gene product, over the use of pure compound.

Mixtures of compounds

Experiment 1

Method

The optimal level of transfection achieved using the compound K3ATL3 had been previously determined as requiring ~5 µM K3ATL3. K3ATL3 was mixed with each of K3ATL1, K3ATL2, K3ATM3, K3ATP3 and K3ATC3 to give a total concentration of lipid of 5 µM in 100 µl at ratios of 0:5, 1:4, 2:3, 3:2, 4:1 and 5:0. K3ATM3 was similarly mixed with K3ATM1, K3ATM2 and K3ATP3. Each of the lipid mixtures was combined with a constant amount of pSVGAL DNA 0.5 µg/well and transfection allowed to proceed normally.

Results

Expression from all wells was low as twice the optimal level of DNA had been used, however there was a strong level in expression in wells containing the combination of K3ATL3 and K3ATM3 in the ratio 4:1, giving a higher level of β-gal expression than either K3ATL3 or K3ATM3 alone (Data not shown).

Experiment 2

This was further tested by making a 4:1 molar mix of the two lipopeptides K3ATL3 and K3ATM3 and testing them in a standard plate assay which involved doubling dilutions of both the lipopeptide and DNA concentration. This was compared to expression achieved with using the pure compound K3ATL3 under the same conditions.

Result

A small but definite increase in expression was achieved using the mix of lipopeptides. At each concentration of lipopeptide tested, the optimal level of transfection agent resulted in a higher level of transfection with the use of the L3/M3 4:1 mix compared to L3 alone at the same concentration.

FIG. 24.

Conclusion

Combinations of lipopeptide transfection agents can achieve superior levels of transfection compared to either of the agents alone. It is expected that further testing along these lines would result in other combinations giving superior levels of transfection to each of the components alone. The results indicate that mixtures of these molecules may have significant effects on their individual transfection properties.

In vivo Transfection

Aim

To determine whether compounds of the formula described can be used to deliver DNA effectively to a whole organism, resulting in expression of the gene delivered.

Method

The plasmid pGFP-N1 (Clontech) encoding the Green Fluorescent Protein, was diluted 10 µg (in 10 µl) into 20 µl 5% dextrose in water and then combined with 2.1 µl of 10 mM K3ATL3 (10% DMSO) in 27.9 µl of 5% dextrose in water. After 10 min incubation at room temperature the mixture was injected into the leg muscle of a hairless mouse. The mouse was sacrificed after 24 hours and the muscle snap frozen on dry ice. Frozen sections of the tissue were made and analysed under the confocal microscope for fluorescence.

Results

Punctate fluorescence was observed in the cytoplasm of muscle cells, and also a very strong fluorescence was seen in the motor end-plates. No fluorescence was observed in tissue sectioned from the uninjected leg.

Conclusion

Preliminary experiments show that effective gene transfer into whole animals can be achieved using these compounds.

The present invention provides an effective way of delivering a compound, in particular DNA into a eucaryotic cell. This method is more efficient than standard $CaPO_4$ style of transfections with some of the embodiments of the present invention being substantially superior to commercially available transfection agents. It is believed that the method of the present invention would be equally useful in the delivery of other compounds such as nucleic acid based pharmaceuticals, such as ribozymes, antisense and the like.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

We claim:

1. A method for introducing nucleic acid into a cell comprising exposing the cell to a compound having the formula:

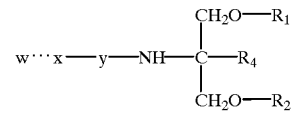

in which:
w is a nucleic acid so that the nucleic acid is introduced into the
x is a peptide or amino acid
y is a linker having a chain length equivalent to 1 to 20 carbon atoms or is absent
$R_4$ is H or $CH_2O$—$R_3$; and $R_1$, $R_2$ and $R_3$ are the same or different and are either hydrogen, methyl, ethyl, hydroxyl or an acyl group derived from a fatty acid having a carbon chain of 3 to 24 carbon atoms saturated or unsaturated, with the proviso that at least one of $R_1$, $R_2$ and $R_3$ is an acyl group derived from a fatty acid.

2. The method as claimed in claim 1 in which y is present.

3. The method as claimed in claim 1 in which the nucleic acid is DNA, RNA or oligonucleotides of either DNA or RNA, modified oligonuleotides or a combination thereof.

4. The method as claimed in claim 1 in which $R_1$, $R_2$ and $R_3$ are the same.

5. The method as claimed in claim 1 in which $R_1$, $R_2$ and/or $R_3$ are acyl derivatives of fatty acids selected from the group consisting of palmitate, myristate, laurate, caproate, oleate and cholesterol.

6. The method as claimed in claim 5 in which $R_1$, $R_2$ and/or $R_3$ are acyl derivatives of myristate or laurate.

7. The method as claimed in claim 1 in which the cells are animal cells.

8. The method as claimed in claim 7 in which the method is conducted in vivo.

9. The method as claimed in claim 7 in which the method is conducted in vitro.

10. The method as claimed in claim 9 in which the compound is administered topically, intravenously, intramuscularly, by inhalation, injection, orally or by suppository.

11. The method as claimed in claim 1 in which the cells are plant cells.

12. The method as claimed in claim 1 in which the compound is present in a liposome or mixed with another lipid.

13. The method as claimed in claim 1 in which the compound contains a linker group "y" having a chain length equivalent to 3 to 7 carbon atoms.

14. The method as claimed in claim 13 in which y is amino butyric, amino caproic or amino caprylic acid.

15. The method as claimed in claim 1 in which x has an overall positive charge.

16. The method as claimed in claim 15 in which x is monolysine, dilysine, trilysine, tetralysine or pentalysine.

17. The method as claimed in claim 1 in which w is covalently attached to x.

18. The method for introducing nucleic acid into a cell comprising exposing the cell to a compound having the formula:

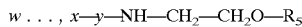

in which:
- w is a nucleic acid
- x is a peptide or amino acid
- y is a linker having a chain length equivalent to 1 to 20 carbon atoms or is absent
- $R_5$ is an acyl group derived from a fatty acid having a carbon chain of 3 to 24 carbon atoms saturated or unsaturated, so that the nucleic acid is introduced into the cell.

19. The method as claimed in claim 18 in y is present.

20. The method as claimed in claim 18 in which the nucleic acid is DNA, RNA or oligonucleotides of either DNA or RNA, modified oligonuleotides or a combination thereof.

21. The method as claimed in claim 18 in which $R_5$ is an acyl derivative of a fatty acids selected from the group consisting of palmilate, myristate, laurate, caproate, oleate and cholesterol.

22. The method as claimed in claim 21 in which $R_5$ is an acyl derivative of myristate or laurate.

23. The method as claimed in claim 18 in which the cells are animal cells.

24. The method as claimed in claim 23 in which the method is conducted in vivo.

25. The method as claimed in claim 24 in which the compound is administered topically, intravenously, intramuscularly, by inhalation, injection, orally or by suppository.

26. The method as claimed in claim 23 in which the method is conducted in vitro.

27. The method as claimed in claim 18 in which the cells are plant cells.

28. The method as claimed in claim 18 in which the compound is present in a liposome or mixed with another lipid.

29. The method as claimed in claim 18 in which the linker group "y" has a chain length equivalent to 3 to 7 carbon atoms.

30. The method as claimed in claim 29 in which y is amino butyric, amino caproic or amino caprylic acid.

31. The method as claimed in claim 18 in which x has an overall positive charge.

32. The method as claimed in claim 31 in which x is monolysine, dilysine, trilysine, tetralysine or pentalysine.

33. The method as claimed in claim 18 in which w is covalently attached to x.

34. The compound having the formula

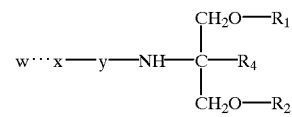

in which:
- w is a nucleic acid
- x is a peptide or amino acid
- y is a linker having a chain length equivalent to 1 to 20 carbon atoms or is absent
- $R_4$ is H or $CH_2O$—$R_3$; and $R_1$, $R_2$ and $R_3$ are the same or different and are either hydrogen, methyl, ethyl, hydroxyl or an acyl group derived from a fatty acid having a carbon chain of 3 to 24 carbon atoms saturated or unsaturated, with the proviso that at least one of $R_1$, $R_2$ and $R_3$ is an acyl group derived from a fatty acid.

35. The compound as claimed in claim 34 in which y is present.

36. The compound as claimed in claim 34 in which w is DNA, RNA or oligonucleotides of either DNA or RNA, modified oligonuleotides or a combination thereof.

37. The compound as claimed in claim 34 in which $R_1$, $R_2$ and $R_3$ are the same.

38. The compound as claimed in claim 34 in which $R_1$, $R_2$ and/or $R_3$ are acyl derivatives of fatty acids selected from the group consisting of palmitate, myristate, laurate, caproate, oleate and cholesterol.

39. The compound as claimed in claim 38 in which $R_1$, $R_2$ and/or $R_3$ are acyl derivatives of myristate or laurate.

40. The compound as claimed in claim 38 in which w is covalently attached to x.

41. The compound as claimed in claim 34 in which the compound is present in a liposome or mixed with another lipid.

42. The compound as claimed in claim 34 in which the compound contains a linker group "y" having a chain length equivalent to 3 to 7 carbon atoms.

43. The compound as claimed in claim 42 in which y is amino butyric, amino caproic or amino caprylic acid.

44. The compound as claimed in claim 34 in which x has an overall positive charge.

45. The compound as claimed in claim 44 in which x is monolysine, dilysine, trilysine, tetralysine or pentalvsine.

46. The compound having the formula:

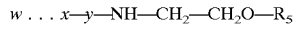

in which:

w is a nucleic acid x is a peptide or amino acid y is a linker having a chain length equivalent to 1 to 20 carbon atoms or is absent $R_5$ is an acyl group derived from a fatty acid having a carbon chain of 3 to 24 carbon atoms saturated or unsaturated.

47. The compound as claimed in claim 46 in which y is present.

48. The compound as claimed in claim 46 in which w is DNA, RNA or oligonucleotides of either DNA or RNA, modified oligonuleotides or a combination thereof.

49. The compound as claimed in claim 46 in which $R_5$ is an acyl derivative of a fatty acids selected from the group consisting of palmitate, myristate, laurate, caproate, oleate and cholesterol.

50. The compound as claimed in claim 49 in which $R_5$ is an acyl derivative of myristate or laurate.

51. The compound as claimed in claim 46 in which the compound is present in a liposome or mixed with another lipid.

52. The compound as claimed in claim 46 in which the compound contains a linker group "y" having a chain length equivalent to 3 to 7 carbon atoms.

53. The compound as claimed in claim 52 in which y is amino butyric, amino caproic or amino caprylic acid.

54. The compound as claimed in claim 46 in which x has an overall positive charge.

55. The compound as claimed in claim 54 in which x is dilysine, trilysine, tetralysine or pentalvsine.

56. The compound as claimed in claim 46 in which w is covalently attached to x.

* * * * *

UNITED STATES PATENT AND TRADEMARK OFFICE
CERTIFICATE OF CORRECTION

PATENT NO. : 5,906,922
DATED : May 25, 1999
INVENTOR(S) : Robert George Whittaker, et al.

Figure 6B:
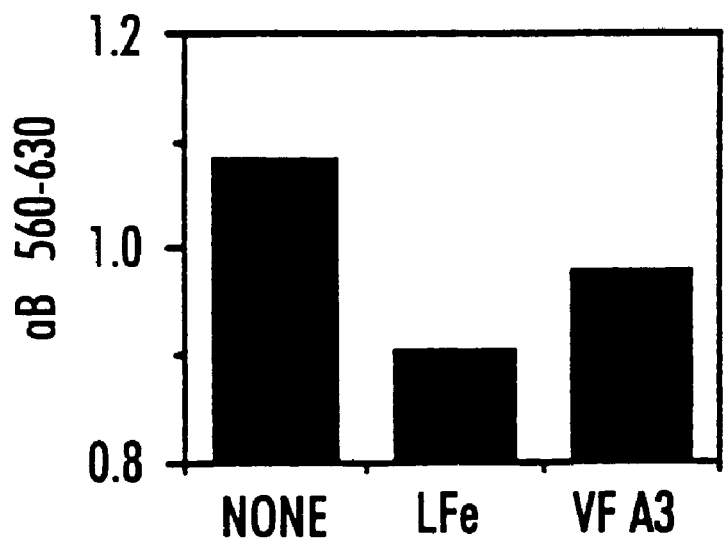

It is certified that error appears in the above-identified patent and that said Letters Patent is hereby corrected as shown below:

Column 4, line 58, change "FIG. 6 shows" to --FIGS. 6A and 6B show--.

Column 5, line 12, change " shows" to --show--.

Column 5, line 22, change " shows" to --show--.

Column 5, line 25, change " shows" to --show--.

Column 5, line 28, change " shows" to --show--.

Column 5, line 32, change " shows" to --show--.

Column 5, line 34, change " shows" to --show--.

Column 5, line 36, change " shows" to --show--.

Column 5, line 41, change " shows" to --show--.

Column 5, line 47, change " shows" to --show--.

UNITED STATES PATENT AND TRADEMARK OFFICE
CERTIFICATE OF CORRECTION

PATENT NO. : 5,906,922

DATED : May 25, 1999

INVENTOR(S) : Robert George Whittaker, et al.

It is certified that error appears in the above-identified patent and that said Letters Patent is hereby corrected as shown below:

Column 5, line 55, change " shows" to --show--.

Column 5, line 62, change " shows" to --show--.

Signed and Sealed this

Twenty-first Day of September, 1999

Attest:

Q. TODD DICKINSON

*Attesting Officer*     *Acting Commissioner of Patents and Trademarks*